(12) United States Patent
Zhang et al.

(10) Patent No.: US 9,740,937 B2
(45) Date of Patent: Aug. 22, 2017

(54) SYSTEM AND METHOD FOR MONITORING A RETAIL ENVIRONMENT USING VIDEO CONTENT ANALYSIS WITH DEPTH SENSING

(71) Applicant: Avigilon Fortress Corporation, Vancouver (CA)

(72) Inventors: Zhong Zhang, Great Falls, VA (US); Gary W. Myers, Aldie, VA (US); Peter L. Venetianer, McLean, VA (US)

(73) Assignee: AVIGILON FORTRESS CORPORATION, Vancouver, British Columbia (CA)

( * ) Notice: Subject to any disclaimer, the term of this patent is extended or adjusted under 35 U.S.C. 154(b) by 607 days.

(21) Appl. No.: 13/744,251

(22) Filed: Jan. 17, 2013

(65) Prior Publication Data
US 2013/0182114 A1    Jul. 18, 2013

Related U.S. Application Data

(60) Provisional application No. 61/587,186, filed on Jan. 17, 2012.

(51) Int. Cl.
*G06T 7/00* (2017.01)
*G06K 9/00* (2006.01)
(Continued)

(52) U.S. Cl.
CPC ........ *G06K 9/00718* (2013.01); *A61B 5/0013* (2013.01); *A61B 5/0046* (2013.01);
(Continued)

(58) Field of Classification Search
CPC ......... G06F 1/3231; G06T 7/20; G06T 19/20; G06T 2207/30232; G06T 2207/30242;
(Continued)

(56) References Cited

U.S. PATENT DOCUMENTS 5,544,649 A    8/1996    David et al.
5,553,609 A    9/1996    Chen et al.
(Continued)

FOREIGN PATENT DOCUMENTS

KR         100234196 B1    12/1999
WO    WO 2012/037157 A2    3/2012

OTHER PUBLICATIONS

Potapova et al, "Calculation of Attention Points Using 3D Cues". Automation and Control Institute Vienna University of Technology.
(Continued)

*Primary Examiner* — Kenny Cese
(74) *Attorney, Agent, or Firm* — Muir Patent Law, PLLC

(57) ABSTRACT

A method and system for monitoring a retail environment by performing video content analysis based on two-dimensional image data and depth data are disclosed. Accuracy in customer actions to provide assistance, change marketing behavior, safety and theft, for example, is increase by analyzing video containing two-dimensional image data and associated depth data. Height data may be obtained from depth data to assist in object detection, object classification (e.g., detection a customer or inventory) and/or event detection.

32 Claims, 21 Drawing Sheets

(51) Int. Cl.
| | |
|---|---|
| H04N 7/18 | (2006.01) |
| A61B 5/00 | (2006.01) |
| A61B 5/107 | (2006.01) |
| A61B 5/11 | (2006.01) |
| A61B 5/1171 | (2016.01) |
| G08B 13/196 | (2006.01) |
| G08B 21/04 | (2006.01) |
| G06T 7/73 | (2017.01) |
| G06T 7/50 | (2017.01) |
| G06T 7/55 | (2017.01) |
| G06T 7/579 | (2017.01) |
| G06T 7/246 | (2017.01) |
| G06T 7/62 | (2017.01) |

(52) U.S. Cl.
CPC .......... *A61B 5/0077* (2013.01); *A61B 5/1072* (2013.01); *A61B 5/1073* (2013.01); *A61B 5/1079* (2013.01); *A61B 5/1113* (2013.01); *A61B 5/1116* (2013.01); *A61B 5/1117* (2013.01); *A61B 5/1128* (2013.01); *A61B 5/1176* (2013.01); *A61B 5/7282* (2013.01); *A61B 5/746* (2013.01); *G06K 9/00087* (2013.01); *G06K 9/00369* (2013.01); *G06K 9/00771* (2013.01); *G06T 7/0016* (2013.01); *G06T 7/246* (2017.01); *G06T 7/50* (2017.01); *G06T 7/55* (2017.01); *G06T 7/579* (2017.01); *G06T 7/62* (2017.01); *G06T 7/73* (2017.01); *G08B 13/19615* (2013.01); *G08B 21/043* (2013.01); *G08B 21/0476* (2013.01); *H04N 7/18* (2013.01); *H04N 7/181* (2013.01); *A61B 2505/07* (2013.01); *G06K 2009/00738* (2013.01); *G06T 2207/10016* (2013.01); *G06T 2207/30196* (2013.01); *G06T 2207/30232* (2013.01)

(58) Field of Classification Search
CPC . G06T 7/0051; G06T 7/0016; G06K 9/00771; G06K 9/00369; G06K 9/6267; G06K 2009/00738; G06K 9/00355; G06K 9/00778; G06K 9/00335; G06K 9/00087; H04N 7/01
See application file for complete search history.

(56) References Cited

U.S. PATENT DOCUMENTS

| | | | |
|---|---|---|---|
| 6,792,319 B1 | 9/2004 | Bilger | |
| 7,516,888 B1* | 4/2009 | Kundu | G06Q 20/00 235/375 |
| 7,801,330 B2 | 9/2010 | Zhang et al. | |
| 7,825,954 B2 | 11/2010 | Zhang et al. | |
| 7,831,087 B2 | 11/2010 | Harville | |
| 7,868,912 B2 | 1/2011 | Venetianer et al. | |
| 7,932,923 B2 | 4/2011 | Lipton et al. | |
| 8,233,660 B2 | 7/2012 | Fritsch et al. | |
| 8,238,607 B2 | 8/2012 | Wang et al. | |
| 8,320,621 B2 | 11/2012 | McEldowney | |
| 9,247,211 B2* | 1/2016 | Zhang | H04N 7/18 |
| 2003/0034971 A1 | 2/2003 | Fujiwara et al. | |
| 2004/0153671 A1* | 8/2004 | Schuyler | G07C 9/00111 726/9 |
| 2005/0094879 A1* | 5/2005 | Harville | G06K 9/00201 382/209 |
| 2005/0201612 A1 | 9/2005 | Park et al. | |
| 2007/0070190 A1 | 3/2007 | Yin et al. | |
| 2007/0127774 A1* | 6/2007 | Zhang | G06K 9/00771 382/103 |
| 2008/0021731 A1 | 1/2008 | Rodgers | |
| 2009/0063307 A1* | 3/2009 | Groenovelt | G06Q 10/087 705/28 |
| 2009/0080711 A1* | 3/2009 | Yokoi | G06K 9/00362 382/116 |
| 2009/0281392 A1 | 11/2009 | Brown | |
| 2010/0197393 A1 | 8/2010 | Geiss | |
| 2010/0199228 A1 | 8/2010 | Latta et al. | |
| 2011/0080336 A1 | 4/2011 | Leyvand et al. | |
| 2011/0134109 A1 | 6/2011 | Izumi | |
| 2011/0143779 A1* | 6/2011 | Rowe | G06Q 30/02 455/456.3 |
| 2011/0200229 A1 | 8/2011 | Tuzel et al. | |
| 2011/0285910 A1 | 11/2011 | Bamji et al. | |
| 2012/0020518 A1 | 1/2012 | Taguchi | |
| 2012/0025989 A1* | 2/2012 | Cuddihy | G06K 9/00369 340/573.1 |
| 2012/0026289 A1 | 2/2012 | Suenaga et al. | |
| 2012/1002630 | 2/2012 | Johnson et al. | |
| 2012/0075464 A1 | 3/2012 | Derenne et al. | |
| 2012/0087572 A1* | 4/2012 | Dedeoglu | G06K 9/00771 382/154 |
| 2012/0087573 A1* | 4/2012 | Sharma | G06K 9/00771 382/154 |
| 2012/0140068 A1 | 6/2012 | Monroe et al. | |
| 2012/0293635 A1 | 11/2012 | Sharma et al. | |
| 2012/0314905 A1 | 12/2012 | Wang et al. | |
| 2013/0041290 A1 | 2/2013 | Kording et al. | |
| 2013/0073093 A1 | 3/2013 | Songkakul | |
| 2013/0182904 A1 | 7/2013 | Zhang et al. | |
| 2013/0182905 A1 | 7/2013 | Myers et al. | |
| 2013/0184592 A1 | 7/2013 | Venetianer et al. | |
| 2013/0184887 A1* | 7/2013 | Ainsley | G05B 15/02 700/291 |

OTHER PUBLICATIONS

Steinbrücker et al, "Real-Time Visual Odometry from Dense RGB-D Images". Department of Computer Science, Technical University of Munich, Germany.

* cited by examiner

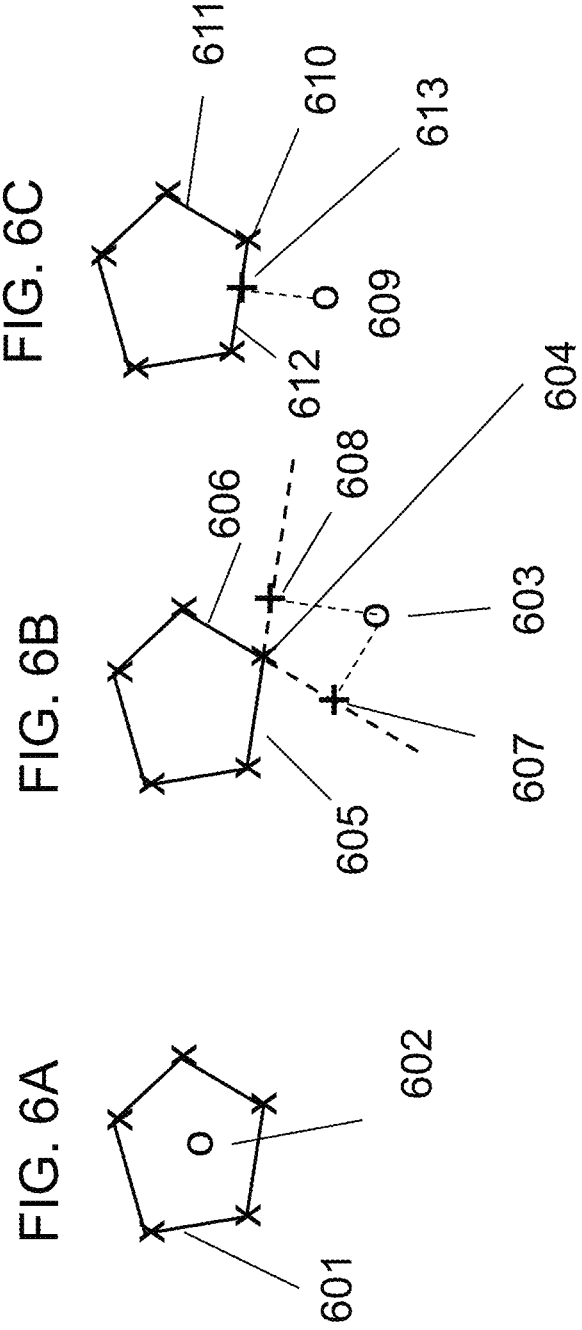

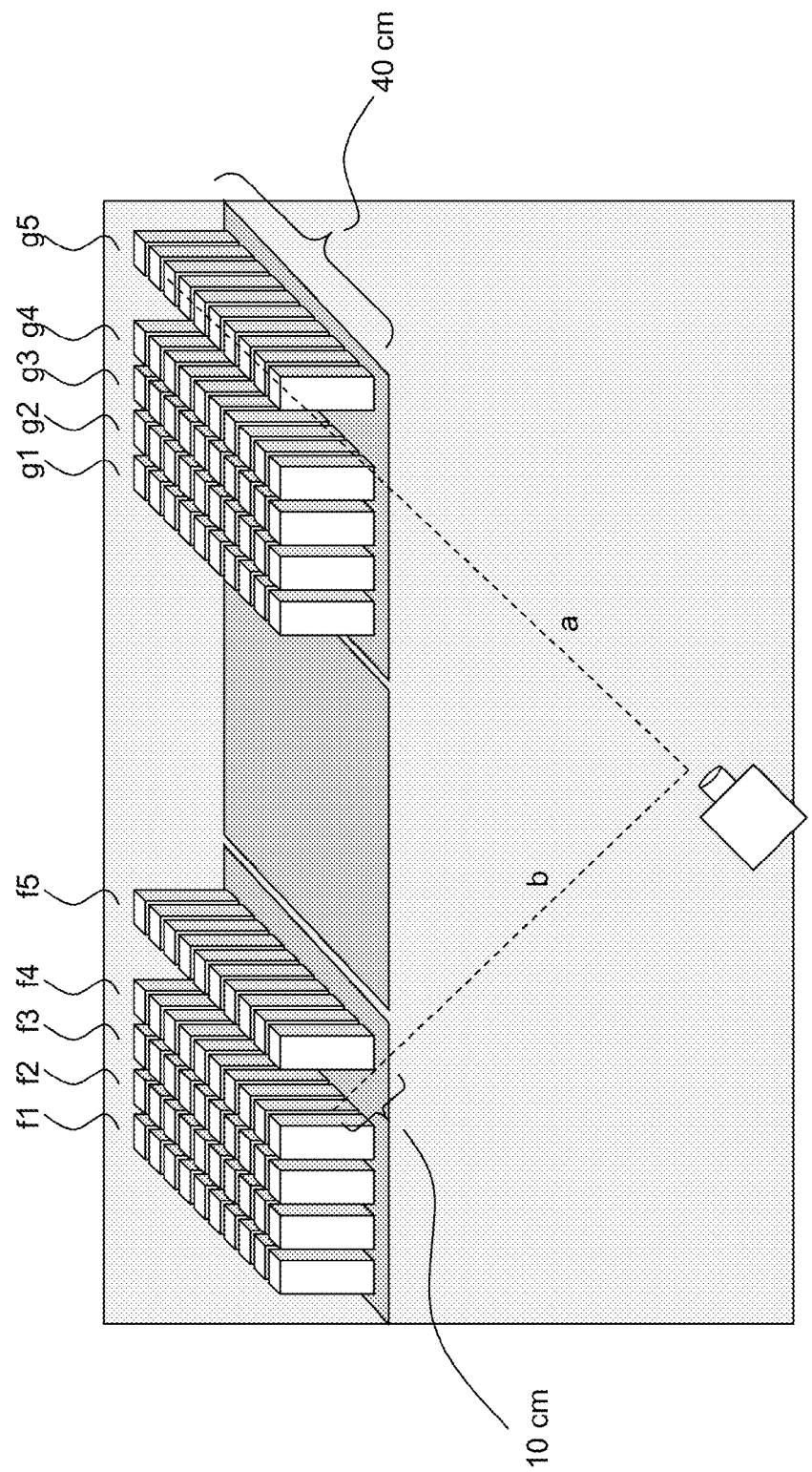

SYSTEM AND METHOD FOR MONITORING A RETAIL ENVIRONMENT USING VIDEO CONTENT ANALYSIS WITH DEPTH SENSING

CROSS-REFERENCE TO RELATED APPLICATION

This application claims the benefit of priority to U.S. Provisional Patent Application No. 61/587,186, filed Jan. 17, 2012, the contents of which are incorporated herein by reference in their entirety.

BACKGROUND

1. Field

This disclosure relates to a system for performing video content analysis (VCA) using depth information to assist retailers in monitoring various aspects of their business, which may help monitor their stores and/or actions of their customers, employees, suppliers etc., help optimize store processes, increase sales, reduce theft and/or increase safety, for example.

2. Background

Use of video to monitor retail environments can be very helpful for a business owner. Video can be reviewed in real time, or later after storage, to track inventory, actions of customers and/or employees, to assist in theft detection, e.g. As the amount of areas and related video to be reviewed increases, it has become impracticable for personnel to constantly review and analyze all recorded video to obtain various information desired by retailers. To assist in this function, video content analysis systems have been designed. In a video content analysis (VCA) system, video streams are automatically analyzed to identify and classify objects, and to determine physical and temporal attributes of the objects. As a result, a log of analytics data may be stored. The analytics data may be used to determine events that occur in real time or at a later time, to aid in searching for objects or detected events, and for other purposes. An example of a VCA system is described in U.S. Pat. No. 7,932,923, issued to Lipton et al. on Apr. 26, 2011 (the '923 patent) and U.S. Pat. No. 7,868,912 issued to Venetianer et al. on Mar. 11, 2011, the contents of each of which are incorporated herein by reference in their entirety.

For example, in a video surveillance system at a grocery store, objects such as customers, cashiers, food items can be identified and related events may be detected to cause notification or some other action in response. For example, customers and cashiers may be identified and their actions reviewed for theft. Shelf space and items (or lack thereof) on the shelf space may be identified to assist in restocking and/or tracking merchandising effects. At an advertising display, objects such as people at the facility can be detected and tracked, and information about the people, such as an amount of time spent by an individual at a particular location, such as the advertising display, at the facility can be collected.

Some existing systems use RGB (red green blue) CMYK (cyan magenta yellow key), YCbCr or other image sensors that sense images in a two-dimensional manner and perform analysis of those images to perform object and event detection. However, identifying objects and related actions using RGB image sensors may be prone to error. For example, a VCA system may make a determination that an object is a human based on an analysis of the shape of the detected object (e.g., the detected object has a certain shape, such as a particular size relationship of a detected torso, head and arm/leg appendages). However, such analysis to determine that an object is a human may equally apply to the shadow of a human in the store. If the VCA system is interested in determining if a customer has slipped and fallen, an improper determination that a shadow is a human object may improperly alert store management to a slip and fall event. Similarly, objects in a shopping cart (e.g., a pumpkin or watermelon) may improperly be identified as a human (e.g., the head of a human).

The embodiments described here address some of these problems of existing retail monitoring systems, and provide use of depth and/or height data to assist in monitoring a retail environment. As a result, a more accurate system and method for detecting and tracking customers, employees and/or inventory, e.g., may be achieved.

SUMMARY

The disclosed embodiments provide a method and system for monitoring retail environments by analyzing video and performing video content analysis using depth data.

In some examples, a method of monitoring a retail environment may comprise taking a video at a store with a video sensor, the video comprising a plurality of frames, each frame including image data; for each frame, receiving depth data associated with the image data, the depth data corresponding to one or more distances from the video sensor to features represented by the image data; analyzing the image data and depth data to detect and classify one or more objects in the store depicted in the video, classification of the one or more objects consisting of at least one of person classification and inventory classification; and detecting an event of the classified one or more objects. In some examples, a method of monitoring a retail environment comprises taking a video at a store with a video sensor, the video comprising a plurality of frames, each frame including image data; for each frame, receiving depth data associated with the image data, the depth data corresponding to one or more distances from the video sensor to features represented by the image data; analyzing the image data and depth data to detect at least one of a presence or absence of one or more objects in the store depicted in the video; and detecting an event of the classified one or more objects. Systems are also disclosed that may perform one or more of the various exemplary methods described herein.

BRIEF DESCRIPTION OF THE DRAWINGS

Example embodiments will be more clearly understood from the following detailed description taken in conjunction with the accompanying drawings. The figures represent non-limiting example embodiments as described herein.

FIGS. 6A-6C show exemplary methods of computing the distance between a pixel and convex null, according to certain embodiments.

FIGS. 18A-18B show another example of an application of a combined calibration and depth detection system such as described in FIGS. 1-12, according to one embodiment.

DETAILED DESCRIPTION

Figure 1:
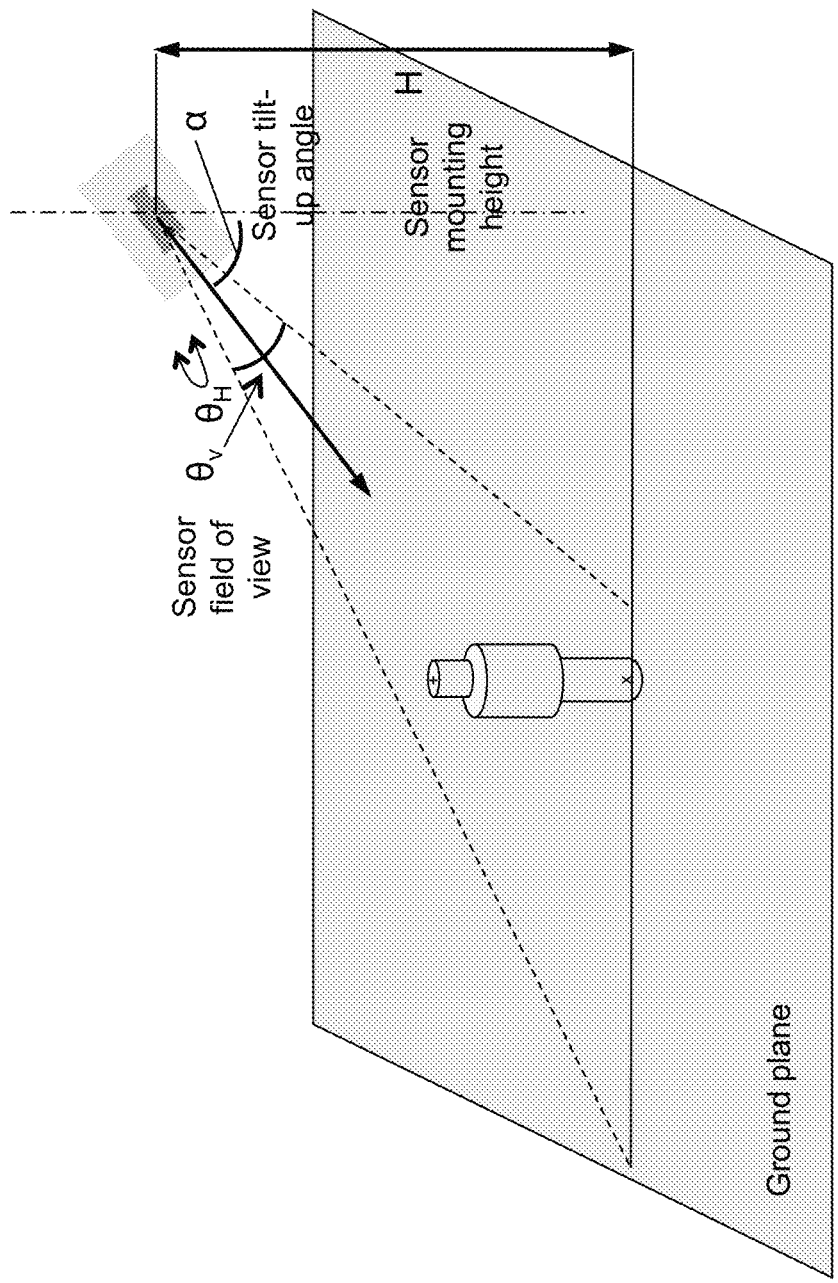
FIG. 1 shows a camera system that can be calibrated to assist in determining the scale and sizes of objects in the field of view, according to one exemplary embodiment.

The present disclosure will be described more fully hereinafter with reference to the accompanying drawings, in which various embodiments are shown. The invention may, however, be embodied in many different forms and should not be construed as limited to the embodiments set forth herein. In the drawings, like numbers refer to like elements throughout.

It will be understood that when an element is referred to as being "connected" or "coupled" to or "in communication with" another element, it can be directly connected or coupled to or in communication with the other element or intervening elements may be present. In contrast, when an element is referred to as being "directly connected" or "directly coupled" or "in direct communication with" another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. Unless indicated otherwise, these terms are only used to distinguish one element from another. For example, a first signal could be termed a second signal, and, similarly, a second signal could be termed a first signal without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

This disclosure includes particular terminology and descriptions that relate to video surveillance and analysis. The descriptions are intended to provide a framework for certain terms and concepts, and are not intended to limit the scope of this disclosure unless explicitly stated.

VCA systems may use cameras that are calibrated in order to detect and identify objects. For example, rather than simply detecting an object based on its relative dimensions, which can represent, for example, a shape of an automobile or a shape of a human being, calibrated VCA systems are able to detect a shape of an object as well as its real-world size. As a result, the system can more accurately detect certain objects. For example, in a non-calibrated system, a VCA system for counting a number of people that appear in a frame of a video stream may count the shapes of both actual people, and of miniature dolls in the frame as people. To avoid this sort of error, VCA systems can be calibrated to provide scale and determine the actual sizes (e.g., actual height and width dimensions) of objects, which improves analysis accuracy.

As one example, FIG. 1 shows a camera system that can be calibrated to assist in determining the scale and sizes of objects in the field of view. To calibrate the camera system, parameters such as camera height (H), vertical and horizontal camera field of view angles ($\theta_H$, $\theta_V$), and camera tilt angle ($\alpha$) can be used. These parameters could be determined by direct measurement, camera specifications, or other calibration processes. For examples of calibration procedures, see the '923 patent, and see also U.S. Pat. No. 7,801,330, issued to Zhang et al. on Sep. 21, 2010, the contents of which are incorporated herein by reference in their entirety. Using these parameters and other information, such as detected outer boundaries of an object (e.g., a top and bottom of a person), the camera system can generally determine the real world size and shape of an object for identification purposes.

However, even a calibrated camera system can have some difficulties detecting real-world objects. For example, to determine an actual height of an object, such as a person, a calibrated system may search for the top of the object (e.g., the person's head) and the bottom of the object (e.g., the person's feet). However, part of a person's body, including the feet may be occluded by one or more objects, such as, for example, by another person, or a shopping cart. In this case, the system may not be able to detect certain information about the person, such as the person's height. For example, if a second person is standing behind a first person, even if the system detects the second person, for example, based on an algorithm that detects human heads or faces, the system may not necessarily know the height of the second person. The second person may be taller than the first person and standing very close to the first person, or the second person may be shorter than the first person, but standing further away from the second person. In either case, however, the camera only sees the first person and the second person's head just above the first person.

Another example where a calibrated system may erroneously detect people or other objects is when shadows or reflections are involved. A calibrated camera system may see a shadow or reflection, and may determine, erroneously, that it is an actual person.

To remedy these problems, in one embodiment, a depth sensor is used together with the calibration information to help determine the real world height or size of an object. The depth sensor information can then be used to supplement, or verify information collected or determined by the calibrated camera system.

As opposed to inferring distance based on geometric equations, certain depth sensors determine the distance of objects from a sensor device by obtaining a direct measurement. For example, the measurement may be made using an infrared projector and a monochromatic CMOS sensor. An exemplary system for determining depth of objects in a three-dimensional space is described in U.S. Patent Application Publication No. 2010/0199228, to Latta et al., published on Aug. 5, 2010, the contents of which are incorporated herein by reference in their entirety. However, depth determination is not limited to the method disclosed in Latta et al., and depth can be determined based on a plurality of different sources, such as lidar, stereopsis, or structured light, for example.

In one embodiment, depth information can be used to supplement camera image information to determine the identity of certain objects. For example, in one embodiment, camera image information can be used to determine all potential human beings in a camera's field of view. For example, a calibrated camera system may be configured to detect objects that are not part of the background (e.g., moving objects) and that have a shape approximately the same shape as a human being. Depth sensor information can then be used to determine a real-world height or size of each object detected as a potential human being, and as a result, the number and location of actual human beings can be more accurately determined, for example, based on the potential human being objects that are above a certain height or that occupy a certain threshold volume. As an alternative, the depth sensor information can be used as a filter to count certain groups of people, for example, if only adults are desired to be counted.

Many methods have been proposed on using depth data to perform scene analysis. In U.S. Pat. No. 8,238,607 and U.S. Patent Application Publication No. 2012/0314905, for example, stereo videos are used to generate disparity map and depth map, and human detection and tracking is performed on the computed depth map. In U.S. Pat. No. 7,831,087, "Plan-View" images are generated from both depth data and non-depth data, and object detection is performed on the "Plan-view" images through "Plan-view" templates. In U.S. Pat. No. 8,320,621 and U.S. Patent Application Publication No. 2012/0197393, a new 3D imaging device RGBD sensor is introduced which can provide both RGB and Depth components for each pixel on the image. Humans and human body parts are detected and tracked on the depth map. In U.S. Patent Application No. 2005/0201612, stereo images are used to produce a height map, the human objects are detected by detecting heads using connect component analysis on the height map. In U.S. Patent Application Publication No. 2012/0293635, the above RGBD sensor is used to detect the head pose, and the head position and orientation are estimated by tracking head features points in 3D space.

Most of the prior art performs the object detection and tracking in the depth space or 3D space. This usually results in a lower resolution and lost details on the objects of interest. Further, the accuracy and quality of the depth data is usually not as good as those RGB image data, and methods of how to deal with the noise and incompleteness of the depth data in the scene analysis have not been well addressed. In addition, processing for object detection and tracking using 3D space data for a whole scene can be computationally complex or even prohibitive. In the present application, a way to use aligned depth data to assist in object detection/tracking under the existing non-depth sensor framework is proposed. The approach is based on the existing RGB image sensor based framework, and uses additional depth information to solve or alleviate certain existing problems. The object detection and tracking is still performed on the traditional non-depth 2D image space, and the depth data is used to provide physical location and size information on objects of interest to help the object detection, segmentation, classification and tracking processes.

Figure 2:
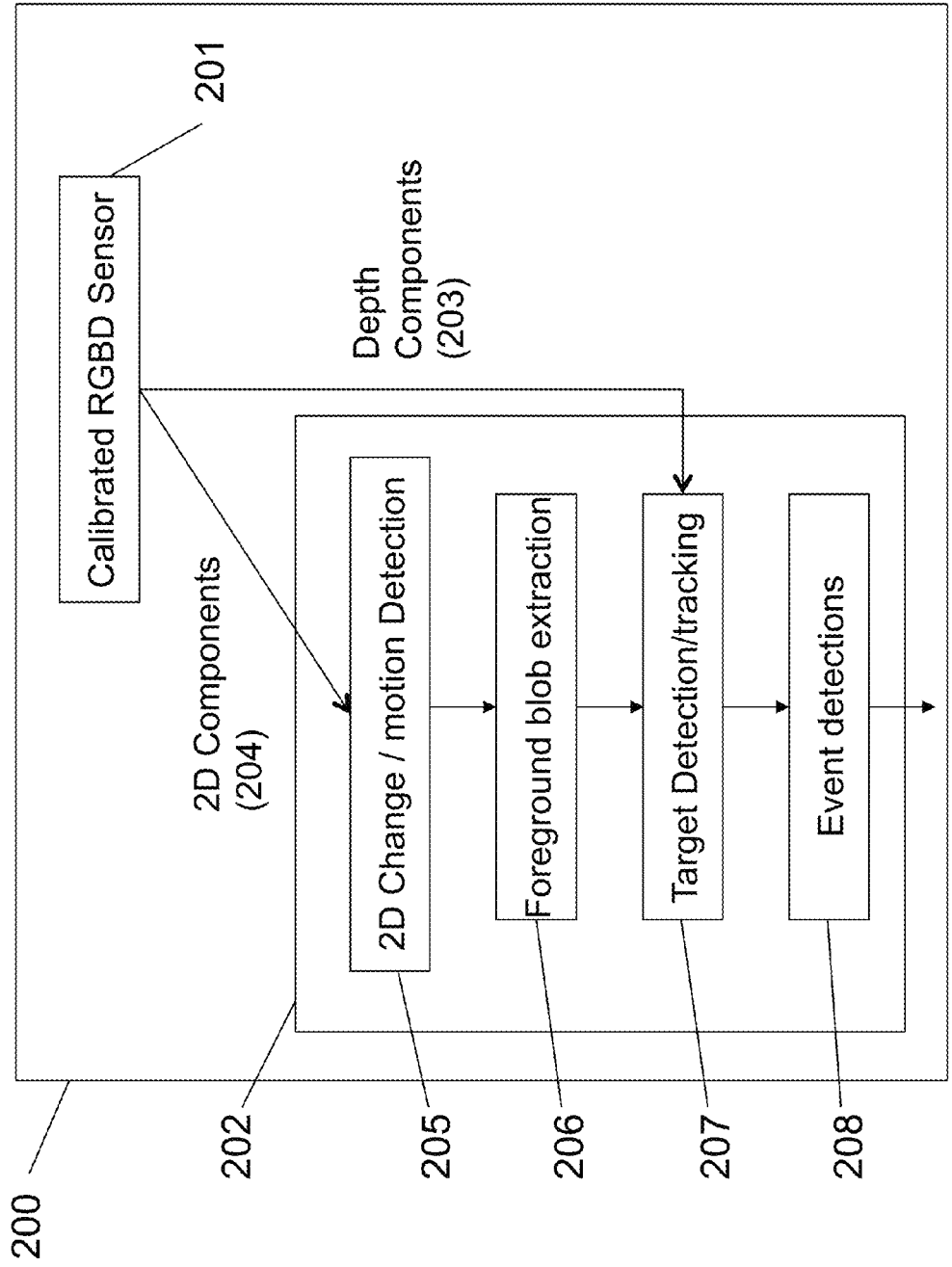
FIG. 2 shows a conceptual block diagram of a video surveillance system and method using one or more sensors that capture two-dimensional (2D) image data and depth data, according to certain exemplary embodiments.

FIG. 2 shows a conceptual block diagram of a video surveillance system 200 and method using, for example, an RGBD sensor or one or more other sensors that capture two-dimensional (2D) image data and depth data. In one embodiment, RGBD video frames are captured by and received from a calibrated RGBD sensor 201. Though one sensor is shown in FIG. 2, video frames may be received from a plurality of sensors. For each image pixel of a video frame, the RGB components and the depth component may be determined. The RGB components and the depth component may come from a same device, like the one introduced in U.S. Pat. No. 8,320,621, or from separated devices and computed through additional procedures, for example, by a disparity map from stereo cameras. Although RGB type data is mainly discussed herein, the 2D image data captured by a camera and used in the video content analysis system and method disclosed herein can be other types of color data or other types of 2D data. RGB is used herein merely as an example.

In one embodiment, the RGB components 204 may be processed by existing video content analysis algorithms, such as like described in U.S. Pat. No. 7,825,954, to Zhang et al., published on Nov. 2, 2010, the contents of which are incorporated herein by reference in their entirety. As such, the system may analyze the 2D (e.g., RGB) components 204 to first perform motion and change detection (step 205) to separate foreground from background. For example, in one embodiment, pixels that are detected as moving are indicated to be foreground data (e.g., by being labeled with a logic value, such as "1"), and pixels detected as non-moving are indicated to be background data (e.g., by being labeled with a different logic value, such as "0"). The output of step 205 may include a foreground mask for each frame. Next, the foreground regions may be divided into separate blobs by blob extraction (step 206). During blob extraction, in one embodiment, the individual foreground pixels are grouped spatially. Foreground pixels that are touching or close to each other are assumed to correspond to the same object and are combined into a single blob. As a result, for each frame, one or more blobs may be detected. Each blob or a part of each blob may correspond to one or more targets at each timestamp (where, for example, a particular timestamp may be associated with a frame of the video). In target tracking step 207 targets may be detected based on the blobs extracted in step 206, and each target may be tracked, where each target may correspond to an object in the scene that is desired to be tracked. The depth component 203 is used here to provide a more accurate determination of which blobs correspond to targets, as opposed to, for example, which blobs correspond to objects that are not targets and do not need to be tracked. Additionally, the depth component 203 may be used to better distinguish different targets from each other. Finally, event detection step 208 performs event detection based on user-defined rules and the targets detected and tracked in step 207. In the embodiments discussed herein, depth-enhanced video content analysis can be performed in real-time, or may be performed on video sequences stored previously, for example, by a DVR, NVR, or other recording equipment attached to a camera, or in a central computer system.

In one embodiment, one or more video cameras/depth sensors may be networked or otherwise in communication (e.g., hard wired or wirelessly) with a server (not shown). Each video camera may include a processor to perform video content analysis of the corresponding video images taken. The content analysis may analyze the two dimensional video image data with the depth information provided by the depth sensor associated with the video camera, and may also analyze the two dimensional video image data alone. On camera processors of each video camera may perform such content analysis to generate video primitives, also referred to herein as metadata, and stream the video primitives/metadata to the server. The video primitives/metadata may represent detected objects, detected classification and/or characteristics of the detected objects and/or actions and/or events (e.g., of the detected objects) detected in the corresponding video. The video primitives, or metadata, may be associated with each frame of the video sequence. By way of example, see U.S. Pat. No. 7,868,912 issued to Venetianer et al. and U.S. Pat. No. 7,932,923 issued to Lipton et al. for exemplary details of video primitive (or metadata) generation and downstream processing (which may be real time processing or later processing) to obtain information from the video, such as event detection, using the generated video primitives. Depth data associated with the video image data may be provided to the server as metadata along with other metadata. Alternatively and/or in addition, height data derived from the depth data (e.g., from on camera processing) may be provided to the server as metadata along with other metadata. The depth metadata and/or height metadata may be associated with detected objects and may include depth and/or height of multiple elements of the detected object. The depth and/or height data and other metadata obtained from on camera processing of the video image data of the corresponding video camera may be streamed to the server.

Alternatively, the one or more video camera/depth sensors may provide recorded video and associated depth data to the server or another computer without processing. In this example, each camera may stream to a server or to another computer the video image data together with the depth data. The server or the other computer may then process the video image data and depth data provided by the video cameras/depth sensors. Such processing may also generate metadata derived from the video image data and depth metadata and/or height metadata as described previously.

The metadata may be processed to classify objects, and to detect actions and events without reprocessing the original video image data. Upon detecting an action/event of interest, the original video image data may be accessed by a user to verify the action/event detection or to review for other purposes.

As a result of the above steps, the following method may be performed. First, a video sequence that includes a plurality of frames may be captured, for example, by an RGBD sensor, such as a camera having depth detection capabilities. Each frame may include a video image that includes depth-enhanced video data. For each frame, two-dimensional (2D) image data (e.g., RGB data) may be extracted, and also depth data may be extracted. The 2D image data and depth data may then be transmitted to and received by a video content analysis system (e.g., one or more processors executing one or more algorithms for analyzing video content). The 2D image data of the video sequence may then be processed to differentiate foreground data from background data and to detect one or more blobs comprised of the foreground data. The one or more blobs may correspond to one or more real-world objects, and correspond to one or more potential targets. For each detected blob, the depth data may be used to determine whether at least part of the blob corresponds to at least part of a target, or to determine whether to track at least a part of the blob as a target. For example, it may be determined that an entire first blob corresponds to a single real-world object, and so that the first blob is determined to correspond to a first target. Alternatively, it may be determined that a first blob actually corresponds to two different real-world objects, and so part of that first blob is determined to correspond to a first target, and another part of the first blob is determined to correspond to a second target. In a third case, a blob may be determined to correspond to only part of a real-world object, and so that blob and an additional blob may collectively be determined to correspond to a single target.

After it is determined that at least part of a blob corresponds to at least part of a target, the target is tracked and at least one event associated with the target is detected.

As discussed in the examples above, a video sequence may be received that includes a plurality of frames, each frame including a video image. For each frame, image data of the video image and also depth data associated with the video image may be received (e.g., it may be extracted from the video sequence and received by a video content analysis system). The image data may then be analyzed to detect one or more objects depicted in the video sequence (e.g., a blob may be extracted, and the system initially assumes that the blob corresponds to a real-world object in the video sequence, for example, by treating the blob as a potential target). Next, using the depth data along with the one or more detected objects, at least a first object of the one or more detected objects is classified as an object to be tracked. For example the first object may be classified as a person to be tracked, an adult to be tracked, a vehicle to be tracked, etc. The object to be tracked may be treated as a target. Next, tracking is performed on at least the first classified object. Finally, event detection analysis is performed on the first classified object. In certain embodiments, the video content analysis described above is automatically performed by a computer system, such as a video content analysis system.

In one embodiment, the depth data 203 may be used in step 207 to help the target detection and tracking processes. The inputs to step 207 may be foreground image blobs extracted from the video frames based on change and motion detection. Each image blob may include a group of connected foreground pixels representing all or part of a physical object, or multiple physical objects. A correct understanding on what each image blob represents may be important for the overall system performance. The disclosed embodiments use the depth data to help make the correct decision in step 207 regarding which targets to track.

Figure 3:
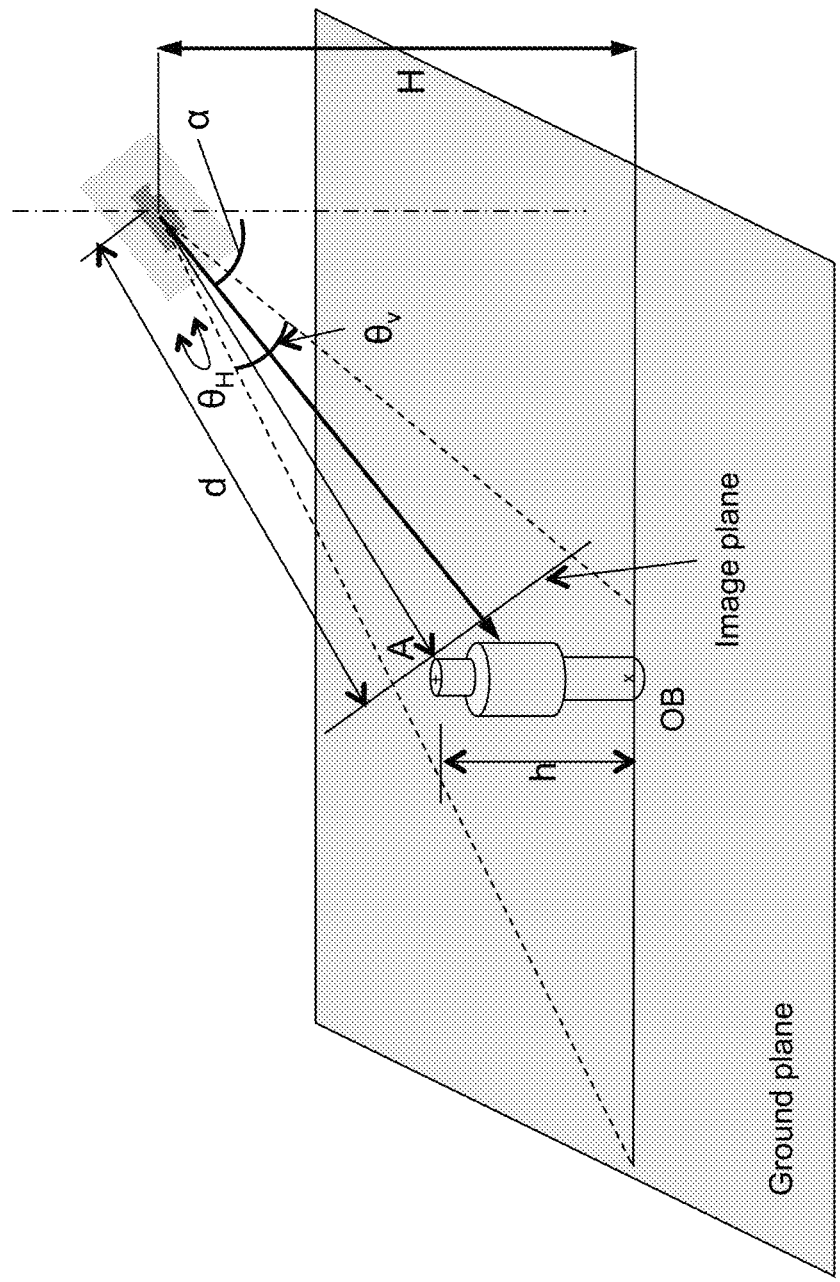
FIG. 3 depicts an example of depth information that can be used in a video content analysis system, according to certain embodiments.

FIG. 3 depicts one example of depth information that can be used to assist in deciding which targets to track. For example, FIG. 3 shows a camera device 301 mounted at a particular location (e.g., a ceiling). The camera device has a particular height (H), vertical and horizontal camera field of view angles ($\theta_H$, $\theta_V$), and camera tilt angle (a). The camera device may include, for example, an image capture portion, such as a standard digital or analog camera, and a depth detection portion, such as an infrared detector as described above, stereo vision technology, or other known devices for directly measuring the depth and distance of objects in a three-dimensional space. In one embodiment, for example, camera device 301 is a calibrated RGBD sensor with a known camera height H, tilt up angle α, and image horizontal and vertical field of views (e.g., known field of view angle and known number of pixels in the field of view). In one embodiment, an object (OB) has a particular shape and a height (h). The height (h) may not be initially known based on 2D data alone. To determine the height, a depth map may be created for the pixels that correspond to a detected blob that represents the person. In one embodiment, each pixel of a blob may be associated with a particular three-dimensional real-world coordinate that indicates the actual location of the object or part of the object that the pixel represents. As such, the distance between the camera and each real-world object represented by one or more pixels can be determined, and using the calibration information and the distance, a height of each pixel or each object represented by one or more pixels can be determined.

As shown in FIG. 3, a three-dimensional coordinate, and thus a real-world height, at point A, which may correspond in one embodiment to the top of a person's head, can be determined by applying geometric equations that include as variables the calibration values (H, α, $\theta_H$, and $\theta_V$) and the distance (d), also referred to herein as depth. As a result of the determined height, additional filtering or analysis can be performed. For example, a better determination can be made as to whether the object is actually a person (e.g., as opposed to a shadow or reflection).

Figure 4A:
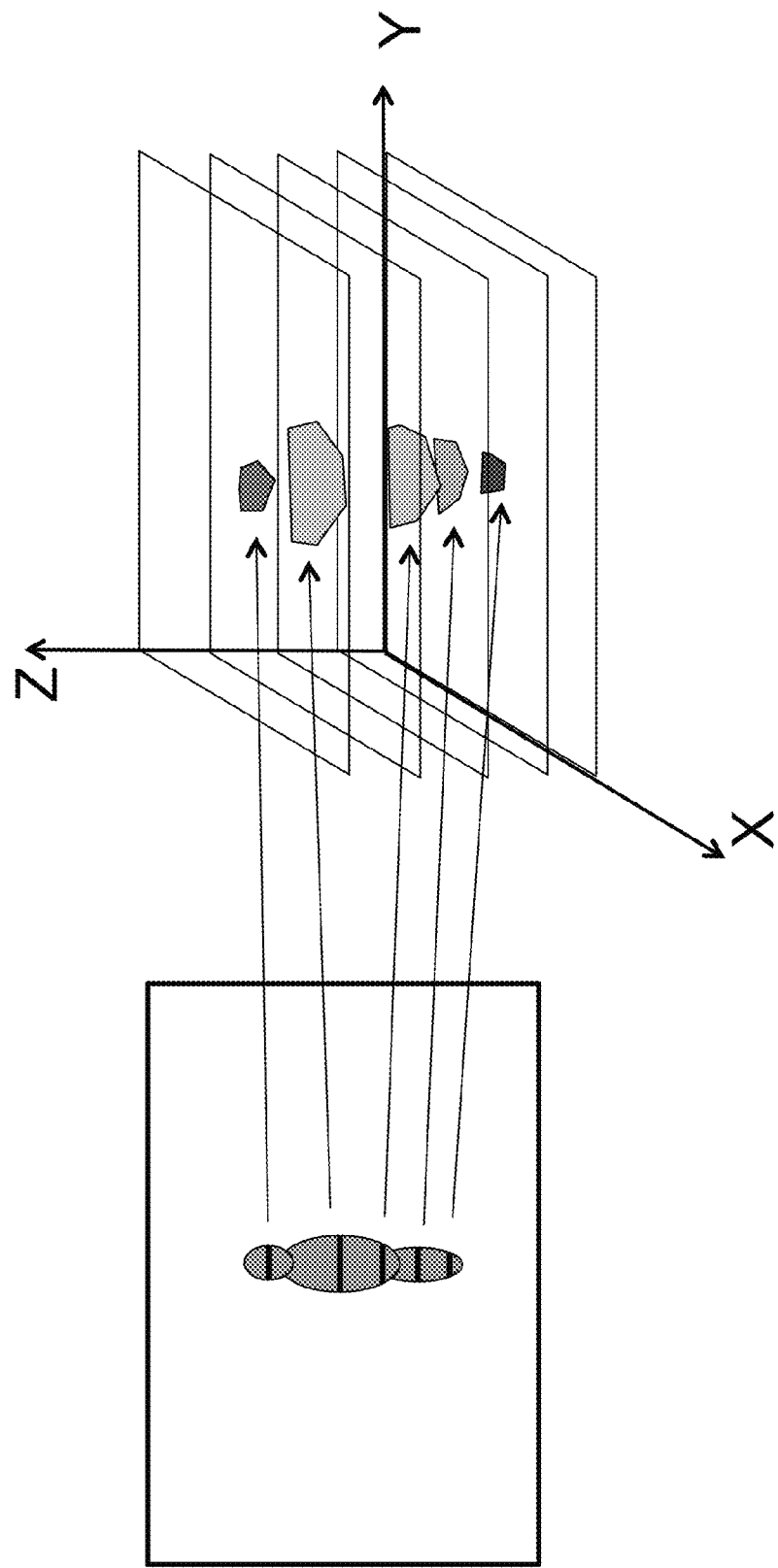
FIG. 4A depicts an exemplary mapping of some samples of image pixels in a blob onto a number of Z-planes in 3D space.

In one embodiment, the physical properties associated with an image blob are estimated by mapping some samples of the image pixels in the blob onto a number of Z-planes in 3D space as illustrated in FIG. 4A. Each Z-plane corresponds to a physical plane parallel to the ground plane. Each point on a Z-plane will have the same physical height in 3D space. The process quantizes the 3D space along the Z axis into a number of 2D planes which are named as Z-planes. The quantization step and the number of Z-planes used may depend on the physical size of the object under investigation. For example, the quantization step can be one foot for human size targets. The quantization step may also depend on some specific requirements of a particular desired detection scheme. For example, if one wants to detect a left behind bag that may be less than one foot in height, a smaller quantization step may be used.

Figure 4B:
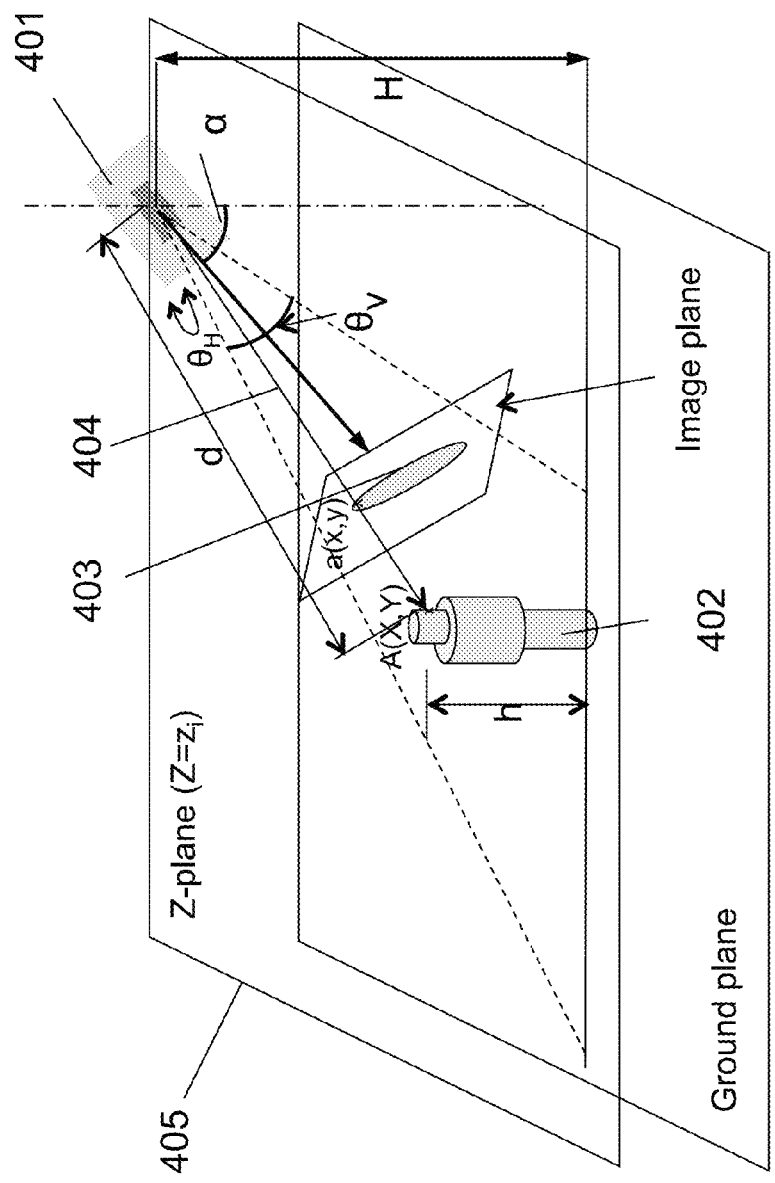
FIG. 4B depicts one example of how to map a pixel in an image blob onto a corresponding Z-plane in physical space, according to one embodiment.

FIG. 4B illustrates one example of how to map a pixel in an image blob onto the corresponding Z-plane in physical space. This mapping method may be implemented using a camera device 401 similar, for example, to that discussed above in connection with FIG. 3. In one embodiment, for example, camera device 401 is a calibrated RGBD sensor with a known camera height H, tilt up angle α, and image horizontal and vertical field of views (e.g., $\theta_H$, and $\theta_V$). Both the RGB image of video frames and the depth measure for each pixel are provided by the sensor. For example, a human object 402 in the view may be detected as an image blob 403 after step 206 of the method 200 in FIG. 2. For one particular pixel a(x,y) in the image blob 403, the positional direction of the pixel from the camera's point of view 404 can be computed based on its image position (x,y) and the known camera horizontal and vertical field of views. This directional information is then combined with the camera height H, the tilt up angle α, and the pixel depth data d to compute the corresponding 3D location (X, Y, h). Once this 3D location is determined, then the point A(X,Y) can be projected onto the closest Z-plane to the height h. The point A(X,Y) becomes one of the sample points of the blob 403 on that plane (e.g., indicated as the $Z_i$-plane 405 in FIG. 4B).

One advantage of the disclosed embodiments is that not every pixel in the RGB image needs to be mapped onto the Z-planes. For example, in one embodiment, only the foreground pixels that represent the image blobs are to be projected onto the discrete Z-planes, and background pixels do not need to be projected onto Z-planes. In addition, because the number of Z-planes mapped is quantized, not every pixel associated with a blob needs to be projected onto a Z-plane. Further, as described further below, convex hulls may be used to represent the object regions on Z-planes. One convex hull may be approximated by a few pivot points, and not every pixel of a blob in a particular Z-plane needs to be sampled in order to form the convex hull. Thus pixel sampling may be performed for each frame and within each image blob to further reduce the computational complexity. In addition, this approach relies less on the accuracy and completeness of the depth data on every image pixel, and is thus more robust despite inaccuracies that may be associated with the depth information.

Figure 5B:
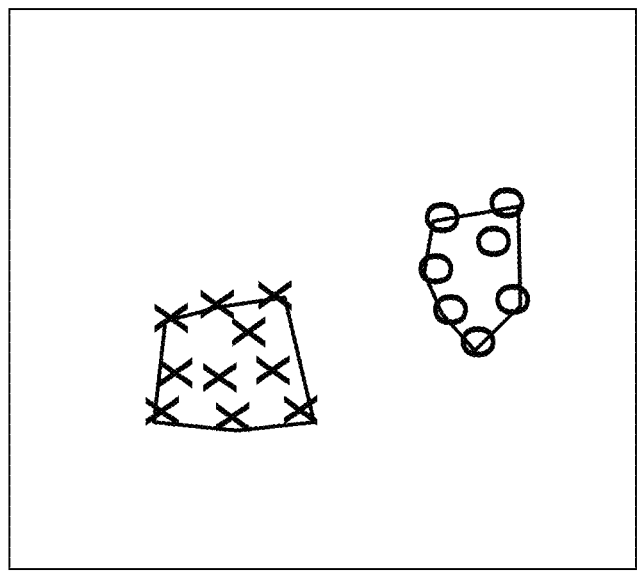
FIGS. 5A-5B show examples of two separate groups of pixels in a Z-plane, according to certain exemplary embodiments.
Figure 5A:
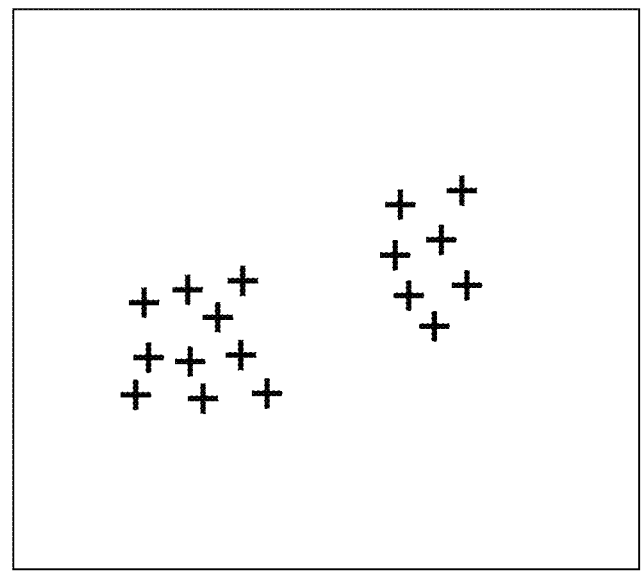

The samples on a Z-plane mapped from the corresponding pixels from the same image blob may form different spatial regions on the Z-plane because they may correspond to spatially separated objects. FIG. 5A shows one example of two separate sample groups on a Z-plane. A clustering process may be used to group these Z-plane samples into separate regions as illustrated, for example, in FIG. 5B. In one embodiment, a fast clustering method using the convex hull blob representation is performed. A convex hull may be used to represent each sample cluster. Its convex boundary defines the object blob on the Z-planes. In one embodiment, the physical distance between a sample and an existing sample or cluster is used to perform the clustering.

FIGS. 6A-6C illustrate an example of a definition of the distance between a sample point and an existing, already-determined convex hull region, and the method to compute the distance. In FIG. 6A, 601 is the convex hull of one existing cluster, 602 is the current sample under consideration, if 602 is inside 601, the distance is considered as 0. If the current sample point is outside of an existing cluster, as illustrated in FIGS. 6B and 6C, the closest pivot point may be searched for first, then the current sample point may be projected on to the two boundary lines which contain the closest pivot point. There are two cases in this scenario, as shown in FIGS. 6B and 6C. In FIG. 6B, 603 is the current sample under consideration, 604 is the closest pivot point, 605 and 606 are the two boundary lines containing 604, and 607 and 608 are the two projection points (e.g., each is the closest point between sample point 603 and its respective boundary line 605 or 606). In this case, both projection points are on the extension portions of the lines 605 and 606, not on the actual boundary of the convex region. The distance to the closest pivot point is then used as the distance to the cluster. In FIG. 6C, 609 is the current sample under consideration, 610 is the closest pivot point, and 611 and 612 are the two boundary lines containing 610. In this case, 613 is the projection point of 609 on 612 and it is on the boundary of the convex hull. Thus the distance between 609 and 613 is considered as the distance between the sample point and the existing cluster. As a result of these calculations, the distance between the sample point 603 and the cluster can be thought of as a minimum distance among (1) the distance between the sample point 603 and a closest pivot point, and (2) a shortest distance between the sample point 603 and a convex hull boundary.

A physical distance threshold may be used to determine whether a sample point outside the cluster should belong to the cluster. Thus the clustering process can be described as follows. Given a list of sample points on a Z-plane (at the same height) that are mapped from sample pixels from an image blob, select a first sample and consider it as the first sample cluster. Then iterate through all the remaining sample points. For a given sample point, compute its distance to all the existing blob clusters. If the distance to a cluster is less than a distance threshold predetermined as a parameter, update this cluster by including this sample into the cluster convex hull. If one sample belongs to multiple clusters, merge all the corresponding cluster convex hulls into a new cluster. If a sample does not belong to any existing clusters, create a new cluster using the current sample. The exemplary method is a one-pass clustering process, and the distance computation only involves a limited number of pivot points. As a result, the clustering process, and the resulting target detection and tracking is computationally efficient.

Figure 7:
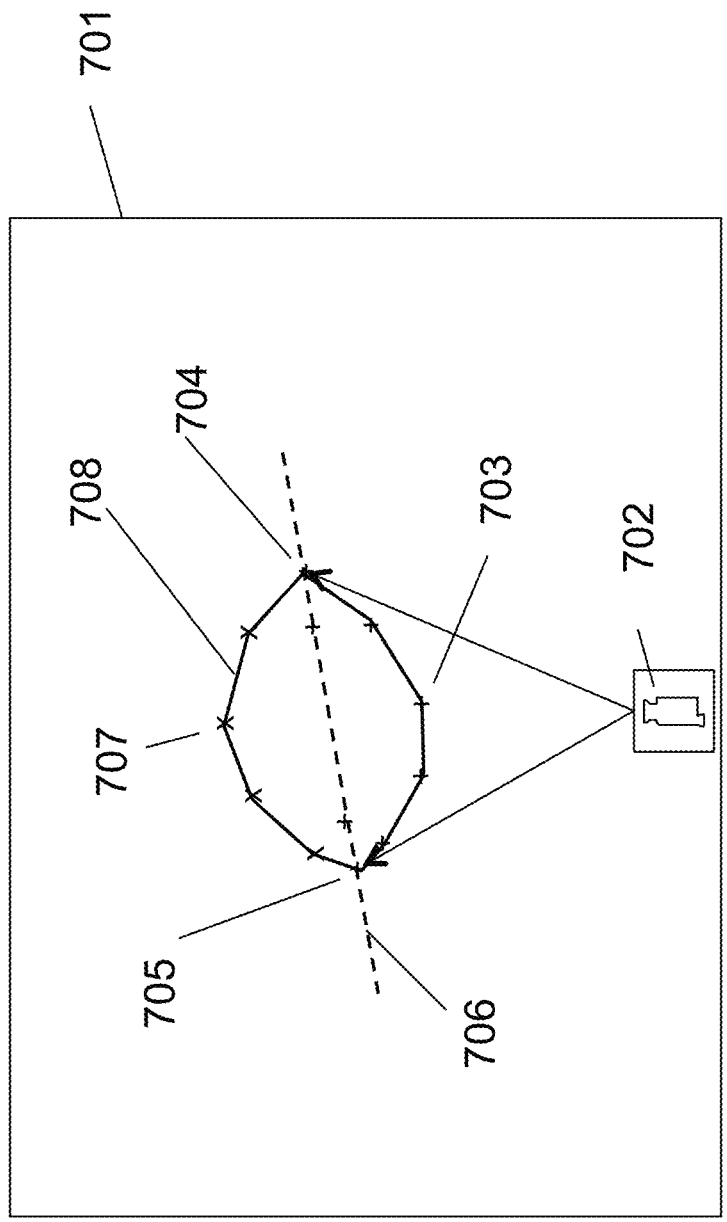
FIG. 7 shows a method of determining a blob convex hull on a Z-plane for one camera location, according to certain exemplary embodiments.

Since a typical RGBD camera is not able to see through an object, a self-occlusion issue often occurs in the 3D space representation of an object. FIG. 7 depicts an exemplary method of addressing this self-occlusion problem. FIG. 7 shows a Z-plane 701 determined based on a camera location 702. The pivot points of an observed convex cluster obtained through the above mapping process are marked as "+". For example, one of these pivot points is indicated as 703. Looking from the camera 702 point of view (wherein the camera is placed a particular distance in the X-Y direction from the object represented by the cluster), 704 is the right most pivot point and 705 is the left most pivot point. These two points are used to determine the self-occlusion line 706. Next, for all the pivot points between the self-occlusion line and the camera, their mirror points on the opposite side of the line 706 are computed and marked as "x", for example, 707 is the mirror point of 703, the final convex cluster 708, is determined by both the original pivot sample points and the mirror sample points. The object self-occlusion is more severe when the camera view is oblique.

Figure 8:
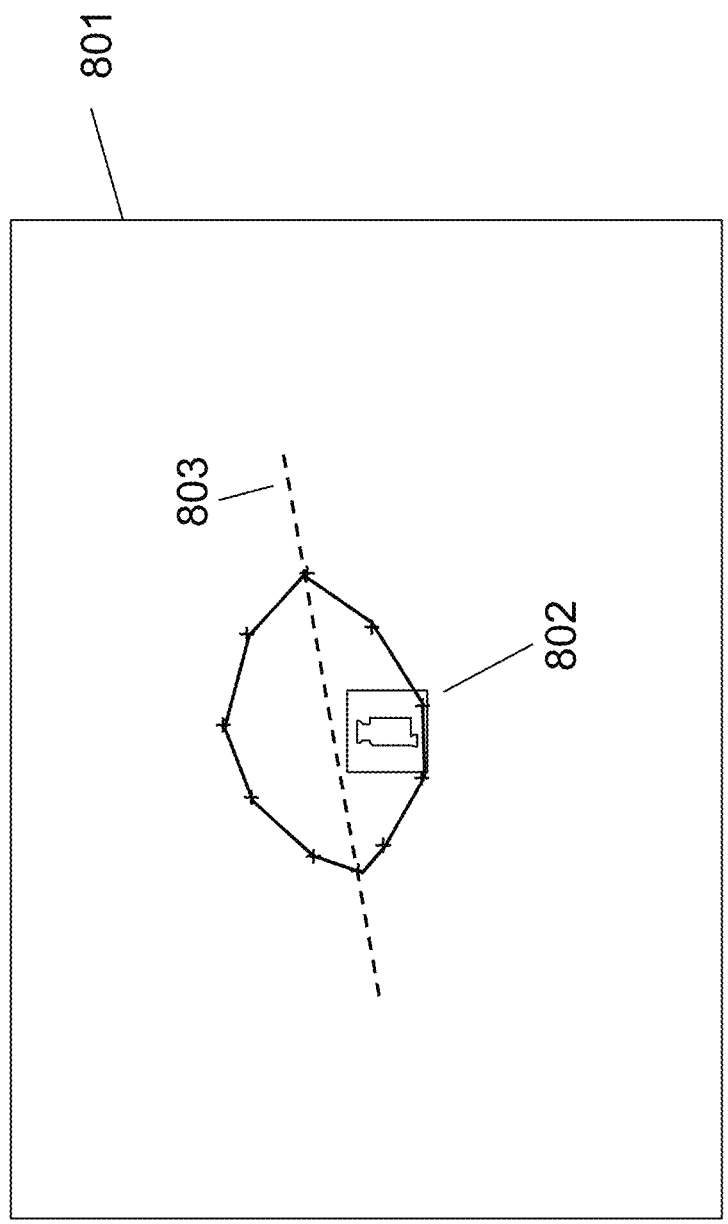
FIG. 8 shows another example of determining a blob convex hull on a Z-plane for another camera location, according to certain exemplary embodiments.

In certain embodiments, a camera position may be directly above part of an object, or almost directly above the object. FIG. 8 shows an almost overhead camera view case, where 801 is the Z-plane, and 802 is the projected camera on the Z-plane. Although there is still a self-occlusion line 803, no extra mirror pivot points are generated because the camera 802 is inside a Z-plane blob cluster and is very close to the self-occlusion line. As described above, the self-occlusion line is the line between a left-most and right-most point, so the self-occlusion line may stay the same for the different camera angles, even though different angles may show more or less 2D image data of an upper surface of an object. Thus, the amount of self-occlusion compensation on each Z-plane is adaptive to the camera position and viewing direction, and this compensation process can provide a more accurate measurement on the projected physical size of the object on each Z-plane.

Figure 9:
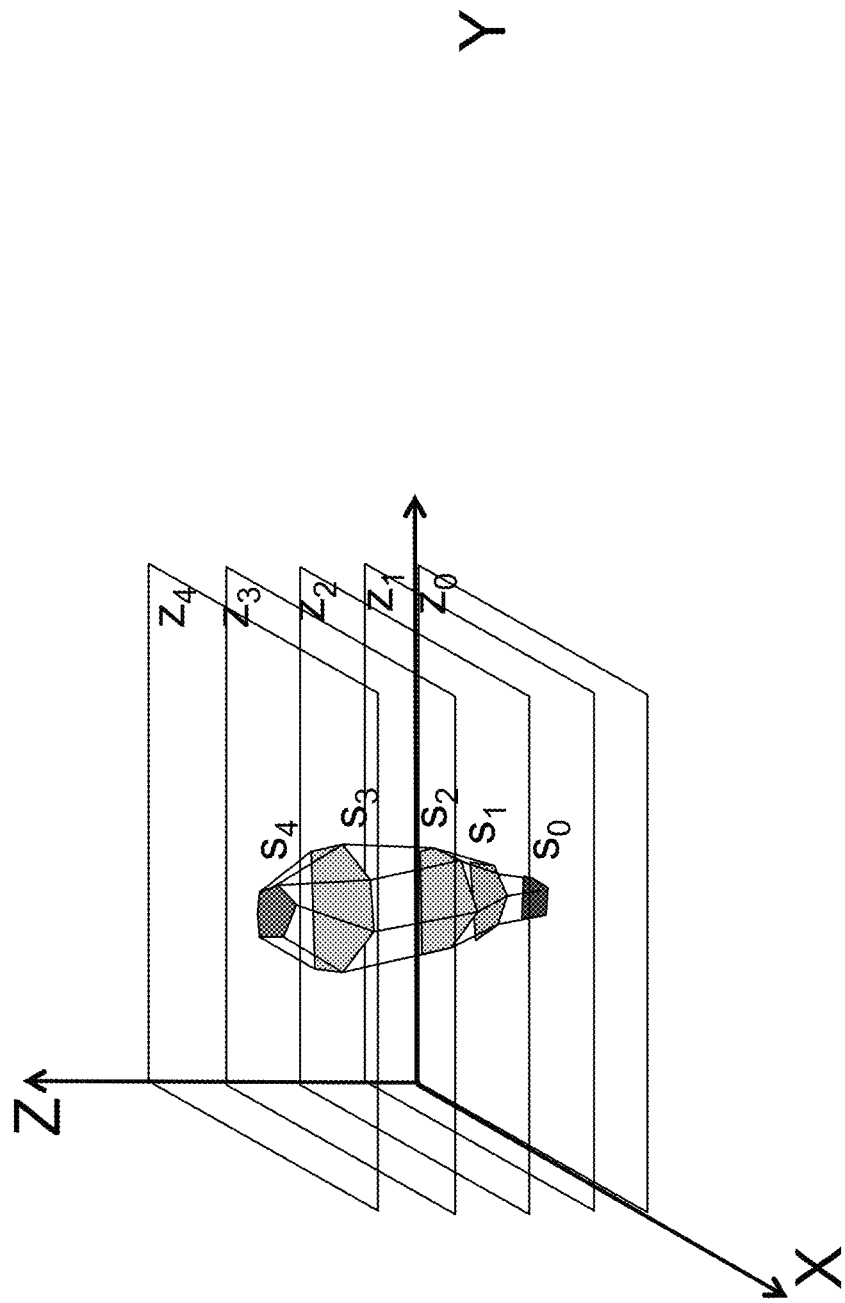
FIG. 9 depicts an example of an image blob and its projected convex hull slices on a list of corresponding Z-plane, according to one exemplary embodiment.

FIG. 9 illustrates an example of an image blob and its projected convex hull slices on a list of corresponding Z-planes. The physical volume of the image blob can be further computed using these convex hull slices on the Z-planes. For a given image blob, assuming there are N Z-planes denoted as $Z_0, Z_1, \ldots, Z_{N-1}$, and on each plane the corresponding convex hull slice area is $S_i$, then the physical volume of the blob can be estimated as:

$$V = \sum_{i=0}^{N-2} (S_i + S_{i+1}) * (Z_{i+1} - Z_i)/2$$

The physical volume measurement may be used, for example, to perform target filtering and target classification. For example, it can increase the confidence on detecting a human object. A human blob should have a physical volume close to an average physical human. The change of human postures will change the image appearance but typically will only have small impact on the human volume. Meanwhile, the human pose change can be detected by tracking the changes of physical height and the projected areas on different Z-planes. The physical height and volume measurements can also be used to distinguishing different types of people from others, such as children from adults.

The physical volume measure may also be used to filter out spurious foreground blobs caused by illumination factors, such as shadows and reflections. These types of non-legitimate blobs usually have little physical volume. The physical height and volume information can be used to detect other types of targets such as vehicles or shopping carts, for example. The physical sizes at different Z-planes are strong clues and may be used to detect objects with different physical size and shapes. Just using a height map without volume information may incorrectly detect a shadow on a wall as a person.

Figure 10:
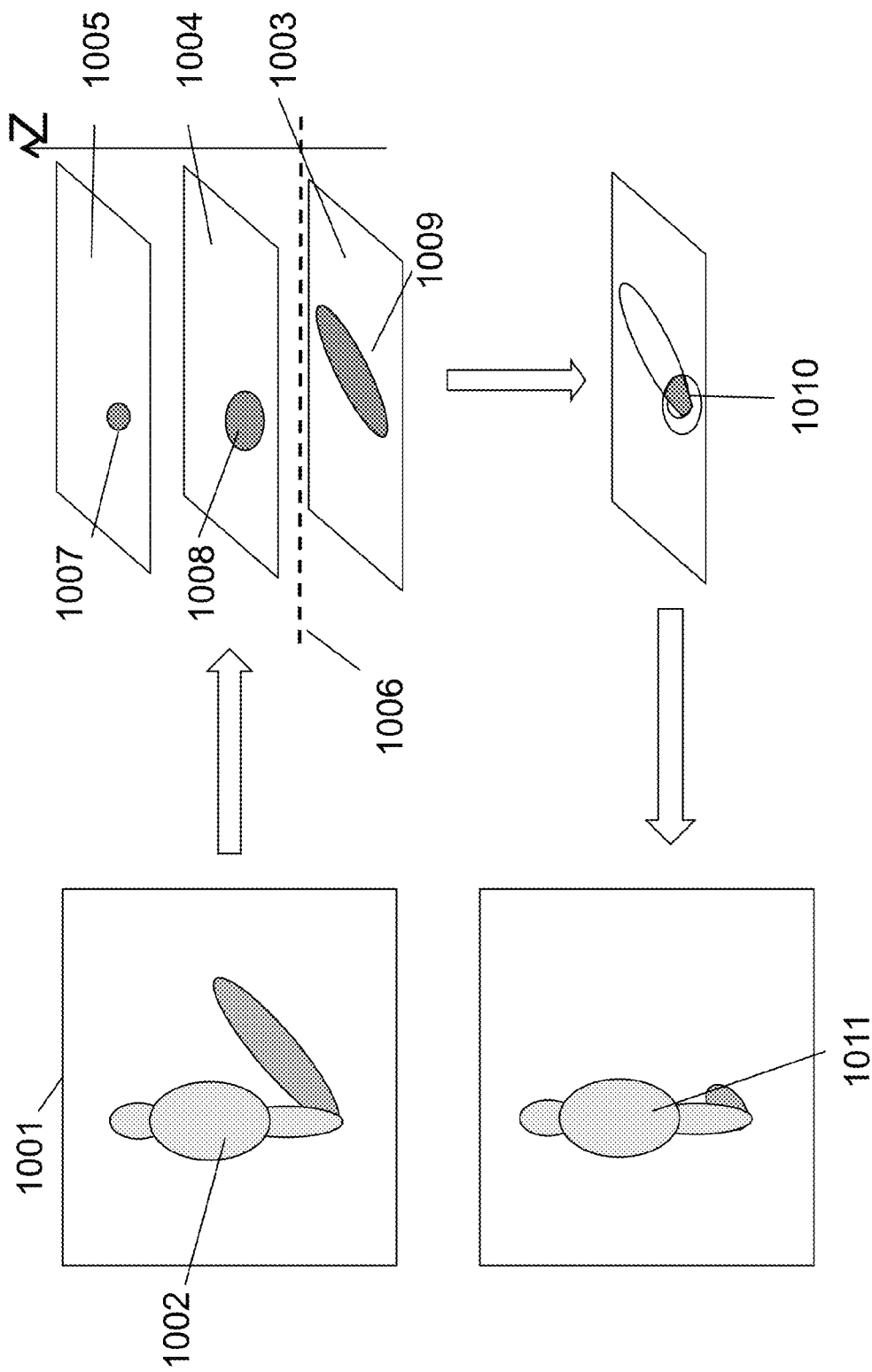
FIG. 10 shows one example of how to remove shadows in an image blob, according to one exemplary embodiment.

FIG. 10 shows one example of how to remove shadows in an image blob. An RGB image 1001 may include a detected foreground image blob 1002, which corresponds to both a human object and its shadow casting on the ground. Without the depth analysis, the system would have difficulty on understanding what type of object the blob represents. Therefore, in one embodiment, to remove the impact of shadow, first, the image blob is projected onto a number of Z-planes indicated as 1003, 1004, and 1005. A height threshold 1006 is used separate the Z-planes into ground plane and non-ground planes. The height threshold 1006 may be slightly higher than the actual height of the ground to take into consideration minor variations of ground height (e.g., non-uniform flooring height, or the addition of carpeting or matts to the floor). For example, the height threshold may be less than one inch or less than two inches above a floor height. The height threshold 1006 may vary over the frame of the image to take into consideration different levels of the floor/ground (e.g., a first height for a parking lot level delivery parking spot and a second height for a warehouse floor height to accept goods from a truck parked in the parking spot). The height threshold 1006 may gradually change over the floor/ground to take into consideration slopes (e.g., a graded parking lot). Blob slices 1007 and 1008 on the non-ground planes, and blob slice 1009 on the ground plane are determined as blob slices for the blob 1002. The blob slice on the ground plane is likely to be a shadow or reflection. Therefore, to remove the potential shadow and reflection from consideration, the blob slices 1007 and 1008 are projected on to the ground plane, for example, from a top-down view. The projected regions create an overlapping region 1010 with the original ground-plane blob slice 1009. The overlapping region 1010 is then used as the estimated blob slice representing the actual object on the ground plane, instead of the original blob slice 1009. Blob regions 1007, 1008 and 1010 can then be projected back onto the image 1001 to refine the original blob 1002 to appear as blob 1011, where most of the shadow part is ignored. The physical volume of the refined blob 1011 can be also computed using 1007, 1008 and 1010.

Figure 11:
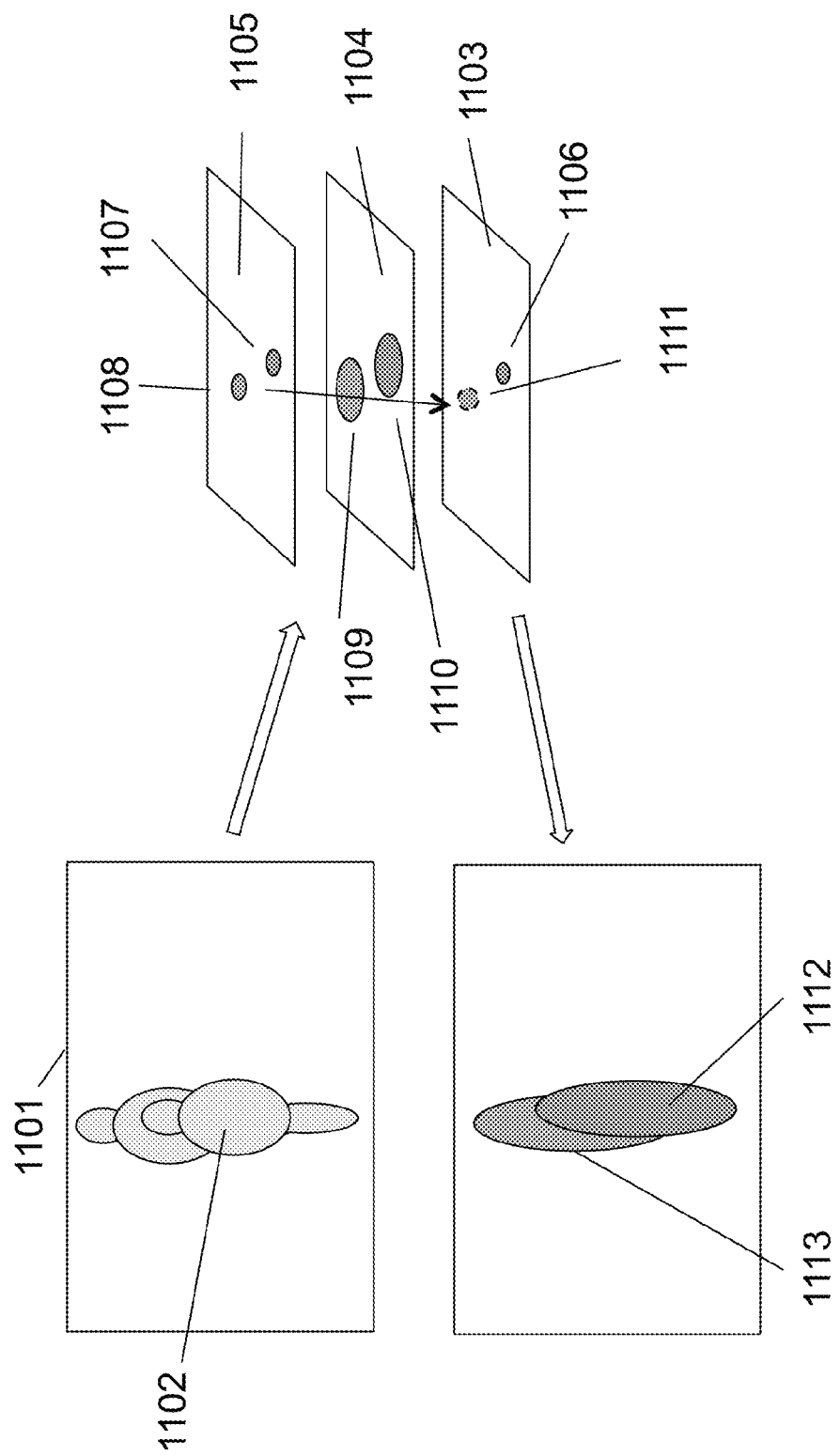
FIG. 11 shows a method of performing blob split on a two-dimensional image using depth information associated with the blob, according to one exemplary embodiment.

Due to the camera viewing perspective, multiple targets not close to one another may be connected in an RGB image and appear as a single blob. In one or more embodiments, they can be separated in the RGB image by using the depth data. FIG. 11 illustrates a method splitting a single blob of an RGB image corresponding to multiple targets using the depth information associated with the blob. An RGB image 1101 includes a detected foreground image blob 1102, which contains two human targets that are separated in physical space. In the RGB image space, however, these two human objects are connected and it is difficult for the system to understand whether there is a single large human target or there are multiple human targets with occlusions. Though techniques like facial recognition may be used in some cases to resolve this question, in some cases, facial recognition may fail (e.g., if the two people have their backs to the camera). By mapping the image blob on to a list of Z-planes 1103, 1104 and 1105, the system may determine that on some Z-planes 1104 and 1105, the two human objects are separated as they are clustered into different blob regions, indicated by 1107, 1108, 1109 and 1110. This is because in reality, the two objects are separated in space. The depth data is used to separate them out on the Z-planes during the video content analysis. This separation in Z-planes provides strong evidence that the image blob 1102 consists of two human objects instead of one. The separated blob regions on the list of Z-planes are then grouped into two physical objects by checking their spatial overlaps. Those regions whose projected region on the ground plane overlaps with each other may be considered to be from the same physical object. For the object (1108, 1109) that does not have a ground plane blob region, the projection from its top plane region 1111 may be used to indicate its ground location. Thus in this example, 1106, 1107, and 1110 correspond to one human object 1112, and 1108, 1109, and 1111 determine another human object 1113 in image 1101. The blob regions of 1112 and 1113 may be obtained by back-projecting their corresponding blob regions on the Z-planes onto the original image. As a result, the physical measurements of the targets represented by the two blobs may be obtained.

Figure 12:
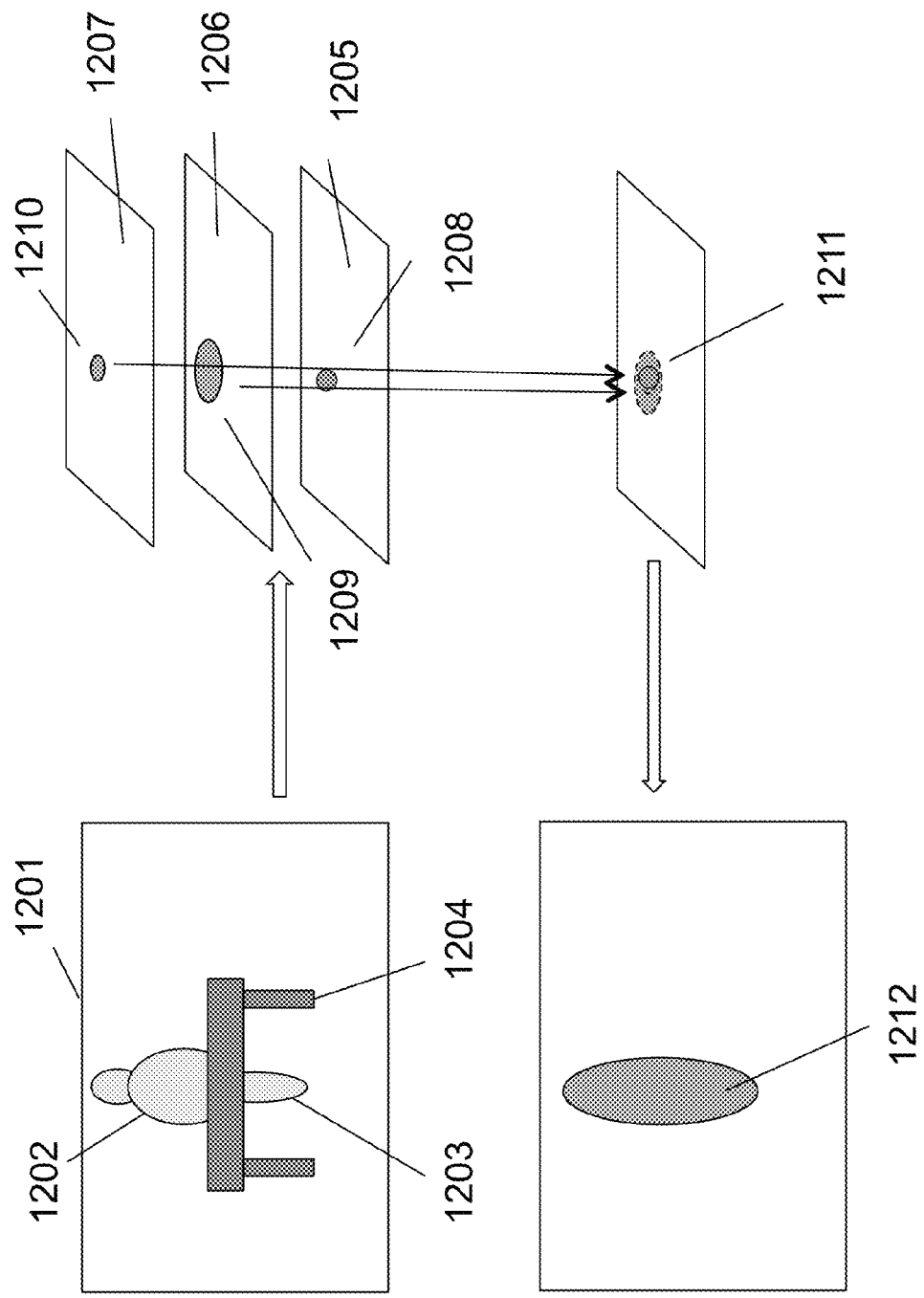
FIG. 12 shows an example of how to merge two falsely separated image blobs, according to one exemplary embodiment.

In some other scenarios, a single foreground object may be occluded by a static background object, or part of the object looks so similar as the background that the system may miss-detect that part as foreground. When these happen, the RGB-based system will likely break a single image object into multiple image blobs. This type of problem may also be solved by the depth analysis. FIG. 12 shows an example of how to merge two falsely separated image blobs, according to one embodiment. An RGB image 1201 includes a static background object 1204 which occludes a human object in the scene and causes the system to detect two separated blobs 1202 and 1203. These two image blobs are projected onto the Z-planes 1205, 1206 and 1207. Blob 1203 has a corresponding blob slice 1208 on Z-plane 1205, while blob 1204 has corresponding blob slices 1209 and 1210 on the other two Z-planes. When projecting these blobs onto the ground Z-plane, they all overlap with one another. Further, the physical volume measured by these projected regions on the Z-planes is very close to that of a human object. This provides strong evidence that 1202 and 1203 actually correspond to a same human object. Thus a blob merge operation may be performed in the image 1202 to create a single blob 1212 which can be classified as a target such as an individual human object.

Figure 13:
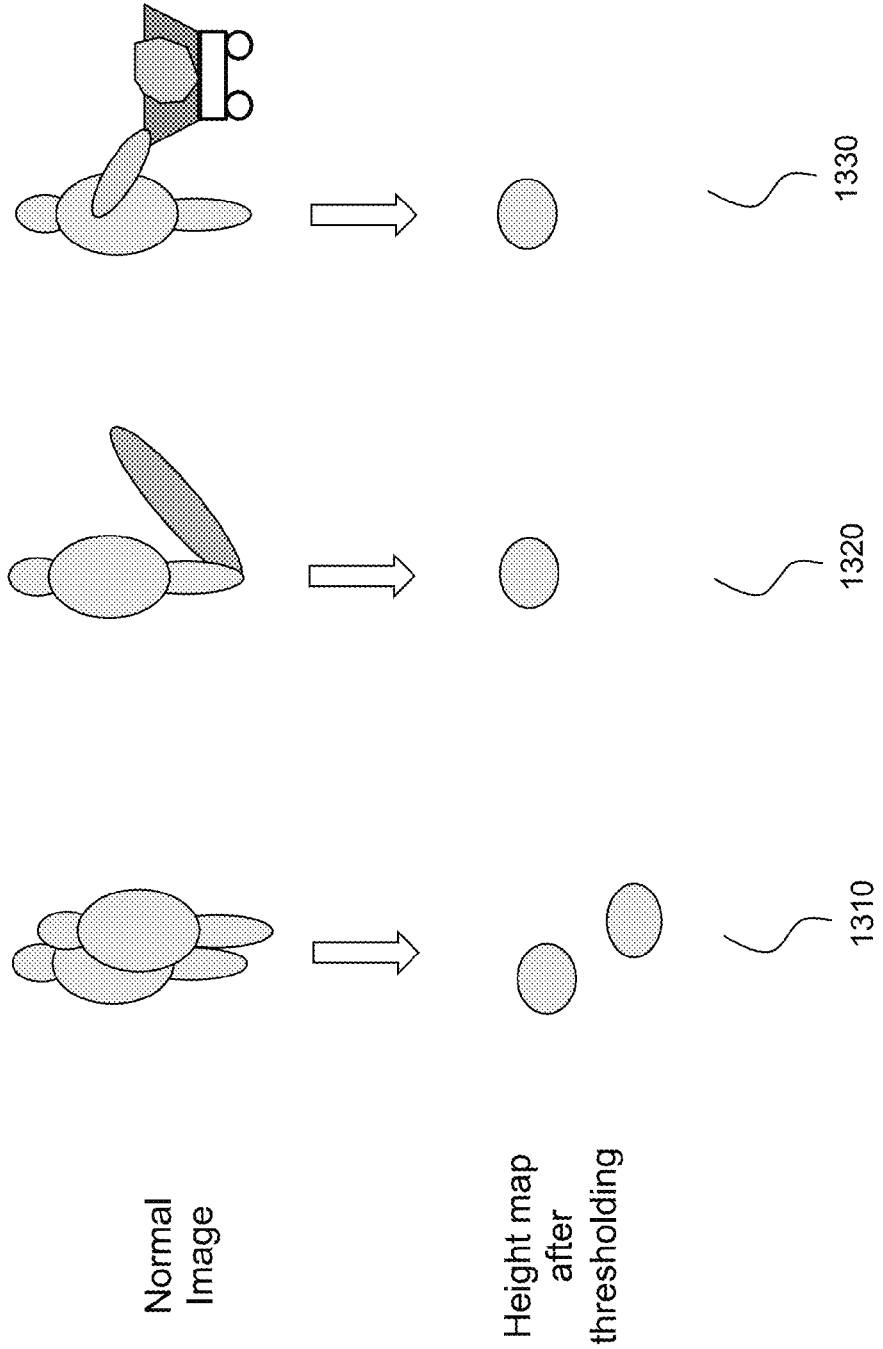
FIG. 13 shows one example of an application of a combined calibration and depth detection system such as described in FIGS. 1-12, according to one embodiment.

One example of a general application of the combined calibration and depth detection system is shown in FIG. 13. As shown in FIG. 13, a height threshold can be applied to detected objects, and can be used to create a target map after the height threshold has been applied. For example, in situation 310, two people stand close together, one occluding part of the other. By applying calibration information and measured depth information to a captured image, a camera device or camera system can determine first that the image is of two targets, and second the height of both targets, and as a result, determines that two people are represented in the captured image. A resulting mapping of the people in the space (a depth map, or height map) can be generated. For example, the mapping may represent a top-down, two-dimensional view of a space, specifically showing the people above a certain height within the space and their location within the two-dimensional view.

In situation 320, however, one person stands in a space, but the person's shadow also appears on the floor. Because the depth detection can be used to remove the effects of the shadow (e.g., as discussed above), the shadow can be omitted from the mapping of people in the space in the depth map. Similarly, in situation 330, one person is partially occluded by a shopping cart, which also has a round object that may be detected as a potential person's head. However, after a height threshold is applied, the person is confirmed to be an actual person and may be tracked. However, after a height threshold is applied, the round object is assumed to not be a person and is not tracked or is tracked as shopping cart objects. Tracking shopping carts and detection of items being added thereto may be used to perform market research and/or determine the efficacy of merchandising (e.g., the effectiveness of advertising, displays, product presentations, product locations, etc.). Tracking shopping carts may be useful to detect theft, such as when a shopping cart has left the store (or other area inappropriate to leave without payment) when the shopping cart contains items and/or when it has not been detected that the shopping cart previously visited a checkout line or otherwise had been associated with payment activities. As a result, only one person is included in the mapping of people after the height threshold has been applied. Alternatively, only one person is mapped as an adult and other objects are mapped with other classifications. In each of these examples (320 and 330) a vision only person counting system (without depth detection) may have counted two people, thus over-counting the number of people in two of the examples.

After objects are identified as targets, those targets may be tracked within a scene in a video. However, because of the height mapping, the tracking may be analyzed from a top-down, two-dimensional perspective, even though there is no camera capturing images from a top-down view looking directly down at the scene. In one embodiment, a standard Kalman filter can be used to track the location of each object.

Figure 14:
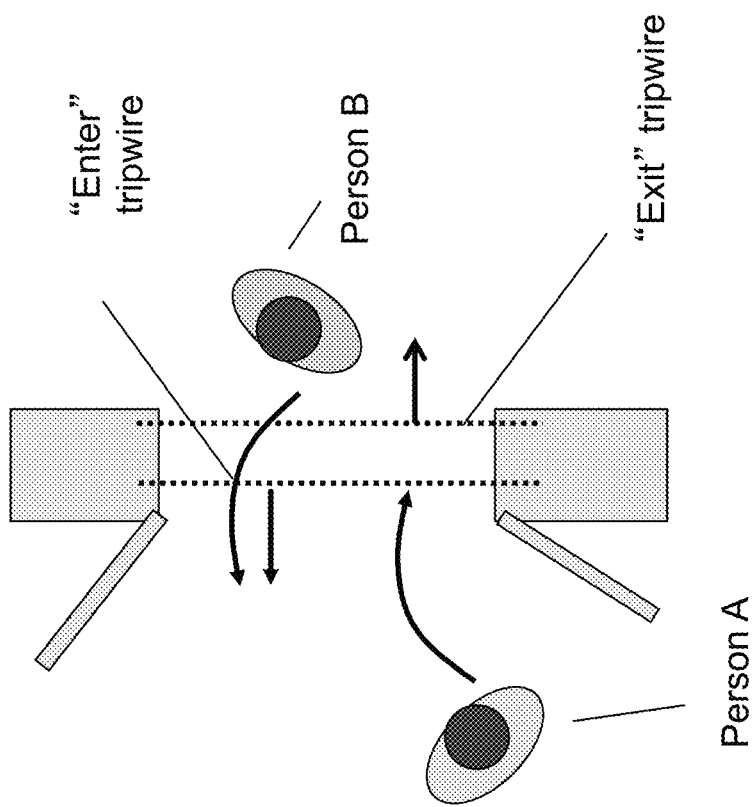
FIG. 14 shows another example of an application of a combined calibration and depth detection system such as described in FIGS. 1-12, according to one embodiment.

Event detection can then be performed based on the detected objects and their tracking information. For example, a virtual tripwire, as described in U.S. Pat. No. 6,696,945, issued to Venetianer et al. on Feb. 24, 2004, the contents of which are incorporated herein by reference in their entirety, can be used to perform counting of people moving in or out of a certain area. An example of a virtual tripwire is shown in FIG. 14.

Figure 15:
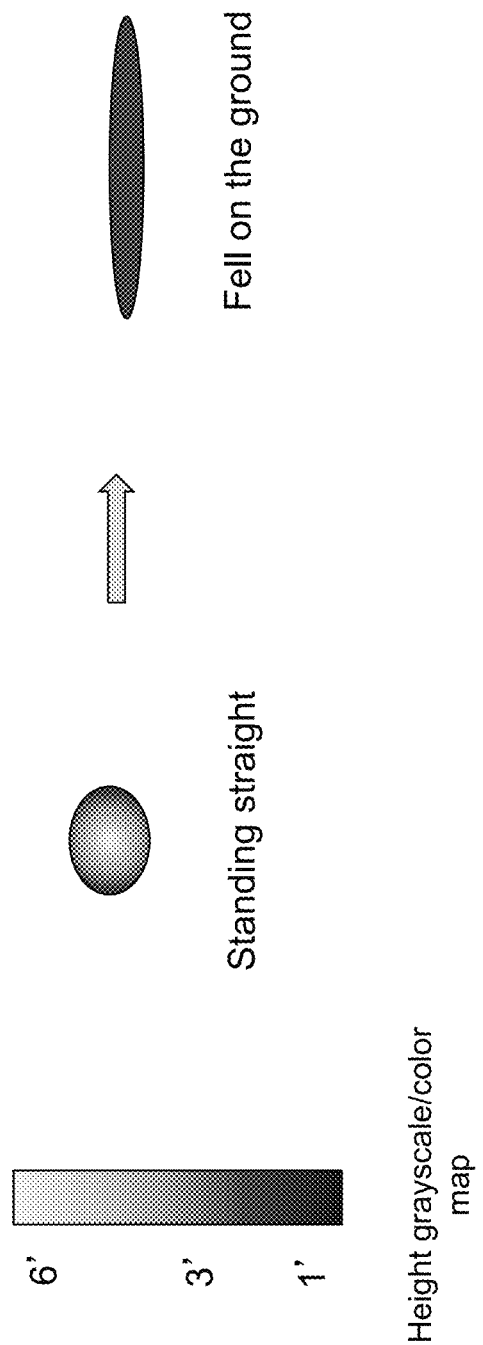
FIG. 15 shows another example of an application of a combined calibration and depth detection system such as described in FIGS. 1-12, according to one embodiment.

Another example of a general application of the above embodiments is to perform object tracking to determine when a person falls down. For example, a captured image may have the shape and size of a person, but the height information (that may be obtained from depth information) may show that the person's head is near to the ground (e.g., one foot off the ground), may indicate that a person has fallen down or is lying down. As a result, the person can be mapped into the two-dimensional overhead view as long and narrow, as shown in FIG. 15. In the two-dimensional overhead view, objects can be represented using a color or grayscale scheme that indicates heights of certain objects, in order to show the topography of the objects in the image. As such, a top of someone's head may have a different shade or color from a point lower on the person's head.

Figure 16:
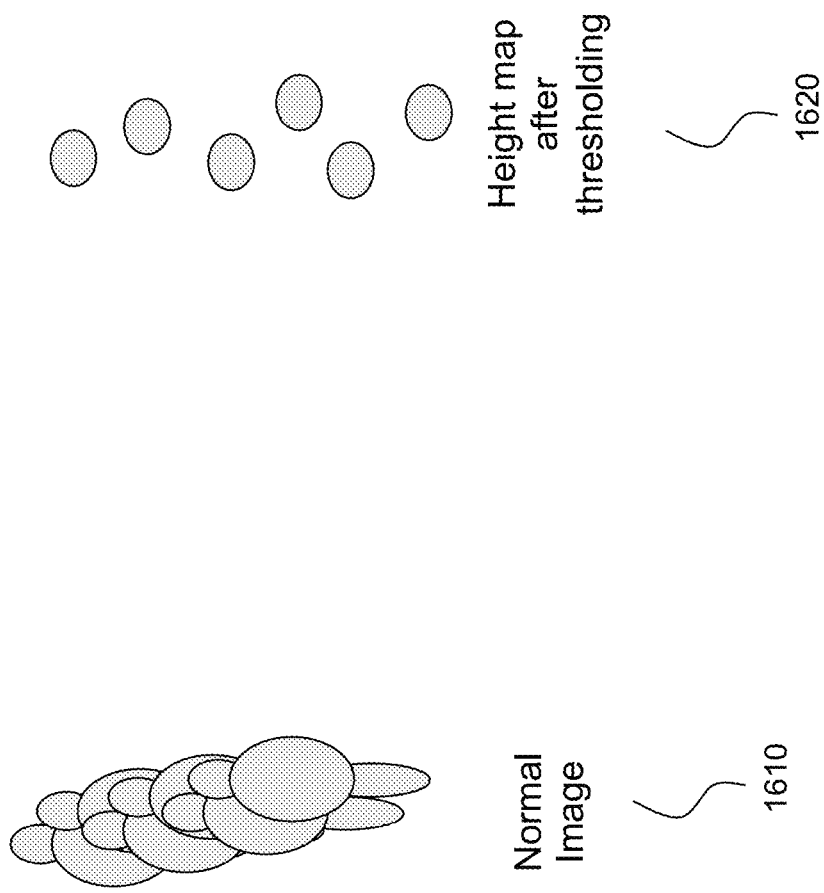
FIG. 16 shows another example of an application of a combined calibration and depth detection system such as described in FIGS. 1-12, according to one embodiment.

In a further example, the embodiments described above, as well as height mapping could be used to more accurately determine queue length (e.g., the number of people waiting in a line). An exemplary queue is shown in FIG. 16. Because many of the people occlude others in the line, or blend in with the other people in the line, standard methods that employ only camera calibration to detect objects may not be able to accurately count or locate the number of people waiting in the line. But with the addition of a direct measurement of distance, for example, for certain pixels of interest in a captured image, a system that uses depth information to verify the classification of potential objects, as well as a height-mapping system can better determine the number of people and their actual location. The actual image (1610) can be then analyzed as a height map (1620).

Figure 17:
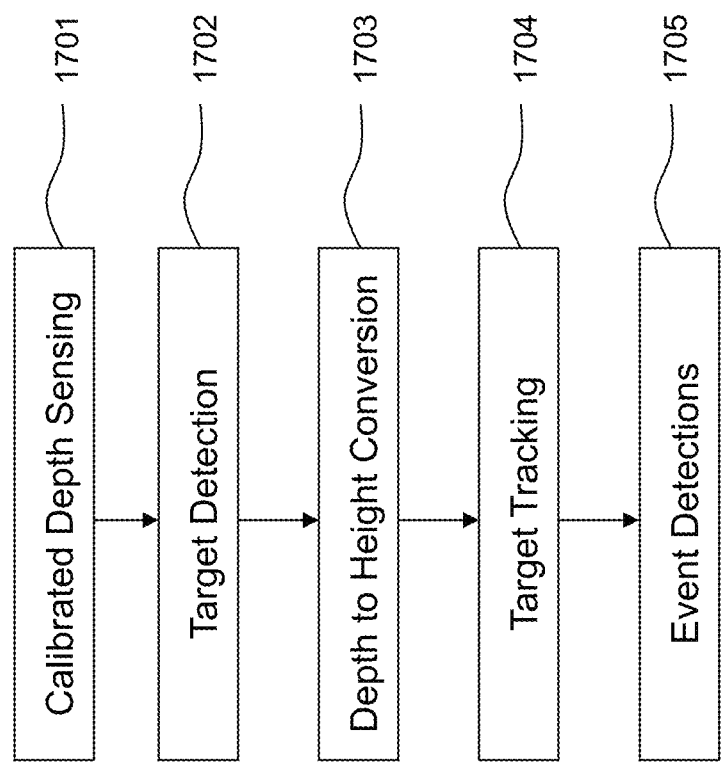
FIG. 17 depicts an exemplary method of performing video content analysis using depth sensing, according to certain exemplary embodiments.

A method of performing video content analysis (VCA) using the disclosed depth sensing VCA system is shown in FIG. 17. As depicted in FIG. 17, in step 1701, calibrated depth sensing is performed. For example, it may be performed by a camera device that employs an image capture portion and a depth sensor portion to determine a depth of certain objects in the captured image. Based on the depth, and/or other information determined based on the depth of pixels associated with certain objects (e.g., foreground objects), targets in a video sequence may be detected (step 1702). The detected targets can then be converted in step 1703 to a height, to determine the height of the object. The height information can then be used to assist in detecting whether the object is a particular target object, such as for example, a person. For example, an analysis component of the system can determine whether the detected object is above a threshold height, and if so, it can confirm the object as a person to be tracked. In step 1704, the target may be tracked. As a result, in step 1705, events can be determined based on the tracked target. Although certain steps in FIG. 17 are described in a particular order, the steps need not follow in that order. For example, in one embodiment, a height map of foreground objects may be determined prior to detecting targets to be tracked, and based on the height map and a height threshold, only certain targets are then selected to be tracked (e.g., a height map may indicate the heights of foreground objects such as people in the scene, and based on a height threshold such as 4 feet, in one embodiment, only adults are selected as targets to be tracked).

Figure 19:
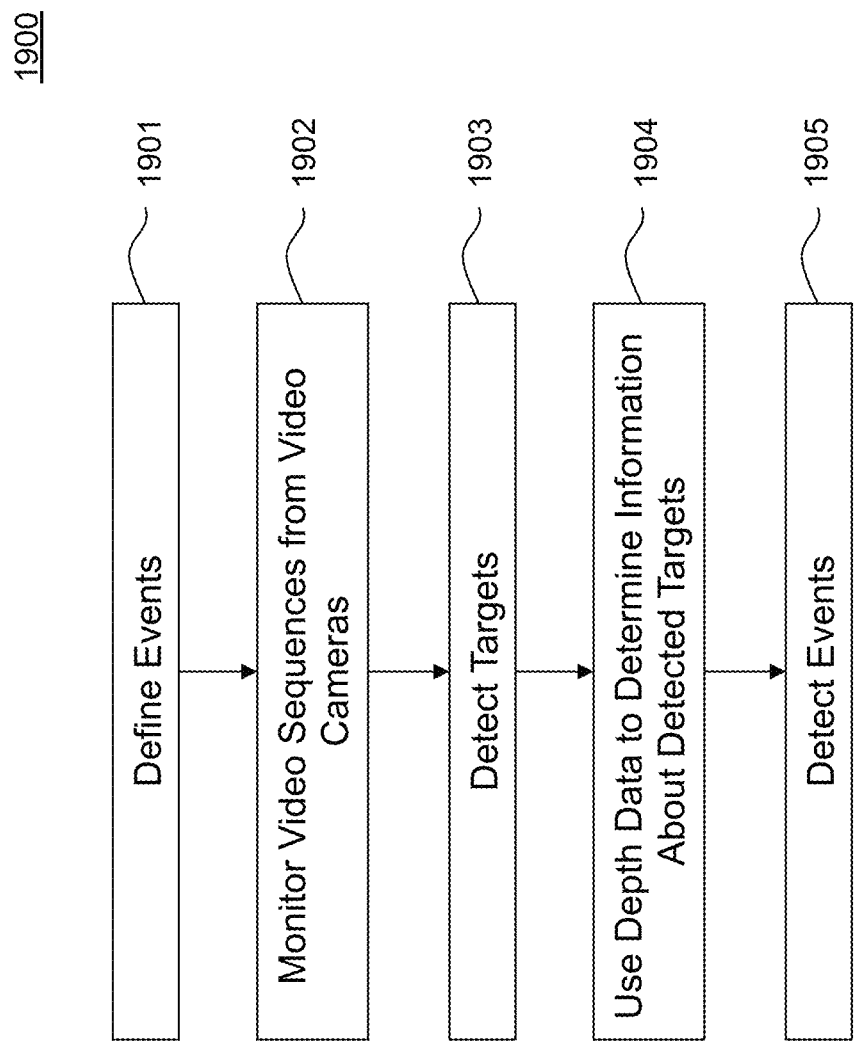
FIG. 19 depicts an exemplary method for monitoring a retail environment, such as a store, using a video content analysis system that uses depth sensing, according to certain exemplary embodiments.

FIG. 19 depicts an exemplary method 1900 for monitoring a retail environment using a video content analysis system that uses depth sensing, according to certain exemplary embodiments.

As shown in FIG. 19, in order to provide automate building actions or alerts, certain events can be defined (step 1901). The events may be defined by a store owner, for example. The events may be defined according to the desires of the store owner. The events may be singular events, such as "spill detected," or may be based on collective information, such as "person detected entering store" or "over 4 people waiting in line at checkout lane number 2". Many events can be set and examples are discussed elsewhere herein and need not be repeated here. Groups of events can be set, and rules can be set based on the events. Events can be set to include information from different locations monitored by different cameras the building. As discussed below, many of the events are more accurately determined by using depth data along with two-dimensional image data to perform depth-enhanced video content analysis.

In step 1902, a plurality of video sequences are monitored from a plurality of video cameras. For example, a plurality of cameras disposed about the store may capture video sequences, two-dimensional image data as well as depth data may be obtained from the video sequences. The data may be obtained by a central computer system (within the store and/or remote), or may be obtained by processing hardware and software in the cameras themselves.

In step 1903, video content analysis steps are carried out on the two-dimensional image data to detect objects in the video sequences. For example, using analysis techniques such as facial recognition and shape analysis, the objects can be identified as particular targets. For example, a person in the video sequences can be identified as a person, or as a particular employee, a particular customer (e.g., "John Smith") or a child.

In step 1904, depth data is used to confirm and/or supplement information about the detected targets. For example, in one embodiment, depth data may be used to determine a height of the target, which in turn can be used to determine a position of the target (e.g., sitting, lying down, standing up). Although step 1903 is depicted as occurring before step 1904, in other embodiments, steps 1903 and 1904 may occur in other order, (i.e., depth data is used to determine what portions of the video to analyze), or simultaneously, such that two-dimensional analysis is performed in conjunction with depth data confirmation to perform depth-enhanced video content analysis.

In step 1905, based on the information obtained in step 1904, an event may be detected (e.g., person detected in area A). Based on the events detected, certain rules can be set that trigger actions, alerts and/or alarms. Different types of and severity levels of alarms can be set based on different types of events.

To implement the system and methods described herein, various computing and optical components may be used, such as one or more of the following: a general purpose computer; supercomputer; a mainframe; a super mini-computer; a mini-computer; a workstation; a micro-computer; a server; an interactive television; a hybrid combination of a computer and an interactive television; a smart phone; a tablet; and application-specific hardware to emulate a computer and/or software. These may include one or more processors, one of more field programmable gate arrays (FPGAs), computer memory, a computer-readable medium such as, for example, any storage device used for storing data accessible by a computer (e.g., a processor may perform various algorithms on data received from a camera device, and a computer memory can then store the information about the various pixels and can store results of blob detection, target detection, and event detection). Examples of a computer-readable medium include: a magnetic hard disk; a floppy disk; an optical disk, such as a CD-ROM and a DVD; a magnetic tape; a memory chip; a solid state storage device; and a carrier wave used to carry computer-readable electronic data, such as those used in transmitting and receiving e-mail or in accessing a network. A tangible computer-readable medium includes computer-readable media, such as listed above, that are physically tangible. In addition, software may be used in combination with the computing and optical components to implement the methods described herein. Software may include rules and/or algorithms to operate a computer, and may include, for example, code segments, instructions, computer programs, and programmed logic. The various computers, cameras, and other image equipment described herein can be connected over a network, which may involve permanent connections such as cables or temporary connections such as those made through telephone or other communication links, and also may include wireless communication links. Examples of a network include: an internet, such as the Internet; an intranet; a local area network (LAN); a wide area network (WAN); and a combination of networks, such as an internet and an intranet. The various hardware and software examples described above are also described in greater detail in the patent documents incorporated by reference herein.

Detecting objects and actions of objects (e.g., events) in retail environments (e.g., grocery stores, clothing stores, etc.) can help managers and store owners make efficient decisions accurately. Using depth as a component of the video content analysis may reduce inaccuracies that affects prior art systems. A number of uses and methods of depth sensing VCA to address various retailers' needs are described below.

Shopping

In one embodiment, the depth sensing VCA system disclosed herein could be used to obtain more accurate people counting within retail stores (e.g., counting people at entries/exits as well as checkout lanes). By removing the impact of shadow, occlusion, and non-human objects (e.g., shopping carts) in the captured images and video, a more accurate counting of people entering or exiting the store, or waiting on line can be achieved. As a result, a retail owner or manager can take appropriate action (calling extra employees to registers, making changes to work schedules, etc.).

For example, in one embodiment, an overhead mounted image sensor (e.g., camera device having depth sensing capabilities) is used, such that a combination of sensor calibration data and depth data can be used to determine the object's physical height. The determined height can then be used to separate human objects from non-human objects. In addition, by using the sensor and calibration information, human head and shoulder patterns can be more reliably detected so that a more robust human occlusion analysis method can be achieved.

In another embodiment, store merchandise can be tracked to determine inventory that needs restocking, items that do not sell well, etc. For example, depth data can be used to create a shelf 3D model, which can provide a measure of items stocked on the shelf space as well as empty space available on the shelf space. As a result, reduced stock or removed stock on shelves can be detected and inventory can be monitored. Similar analysis can be used, for example, in a grocery store on shelves as well as in other areas, such as a meat and dairy counter, a produce section, etc. In one embodiment, a shelf monitoring can be used to determine a shelf clearing action, e.g., when a person takes most or all items from a shelf, presumably with the intention of stealing. In certain embodiments, the placement of the image sensor can be overhead, angled towards the shelves in question or can be opposite the shelf looking at the shelf itself (with the angle of the image sensor perpendicular to the wall or structure on which the shelf resides, or at some offset). The above store merchandise tracking embodiment takes into account the angle of the sensor to the shelf as well as the angles to the shelf locations above and below and left to right of the image sensor.

For example, the depth sensing VCA system can monitor the shelf emptiness change over time. If the monitored shelf emptiness measure increases above a threshold within a certain period of time, the system can set an alarm that a shelf is empty or soon needs to be restocked.

Figure 18B:
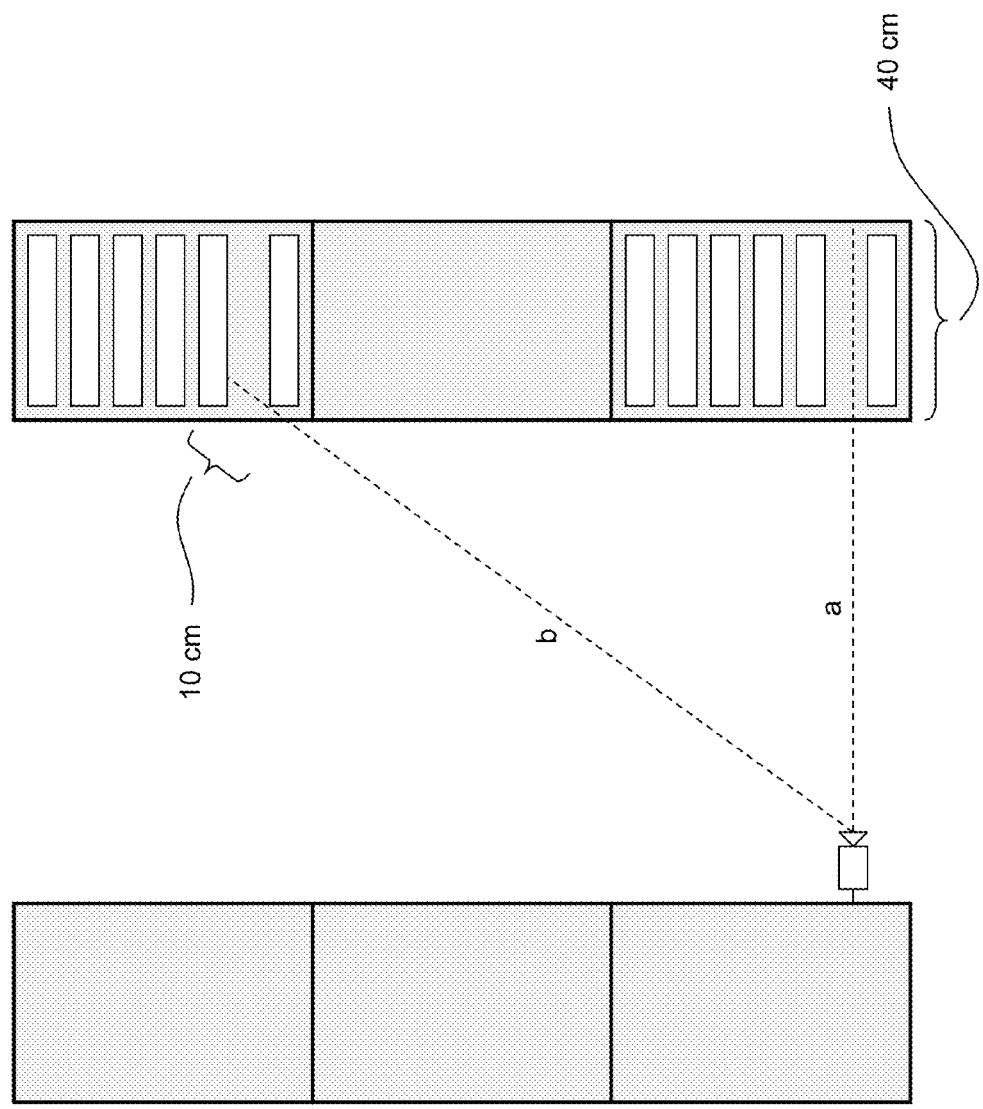

Assuming the sensor is perpendicular to the wall or structure on which the shelf resides, the system can determine emptiness of a shelf location based on measured depths at different locations in the image sensor field of view, within the image sensor's depth detection resolution tolerances. For locations that are not directly perpendicular, the system can take into account the offset angle and distance to determine perspective that may be used to determine the amount of a shelf that is empty. For example, as shown in FIGS. 18A and 18B in perspective and overhead views, looking straight on (a), at the image sensor's central detection point, the system determines a gap of 40 cm between the front of the shelf (shelf "g") and the next object, which is a back wall. Because the gap is above a particular threshold (e.g., a threshold may be set as a known distance between the edge of the shelf and the wall, for example 40 cm) the system detects that an item or row of items at that location on shelf g is missing, so that part of the shelf is empty. However, as the system examines locations surrounding that central point, such as, for example shelf f at the angle shown by (b), the system determines a gap of only 10 cm between the front of shelf f and the next object, which is not the back wall but is the side of an adjacent item (item f4). The gap does not meet the 40 cm threshold, even though part of shelf f is empty. Therefore, the system can account for the total distance from the image sensor to the front of the shelf, as well as the distance between the front of the shelf and the detected object (f4), to determine how many items are missing from the shelf. As a result, the system accounts for a different threshold gap size to take into account perspective based on the distance to the shelf. So in this example, at the image sensor's edges of the field of view, the threshold gap may only be 10 cm to indicate a missing item, or may be 15 cm to indicate two missing items, etc. The example shown in FIGS. 18A and 18B is exemplary only. Other variations, such as different threshold values, sizes or numbers of objects on each shelf or in a row on each shelf, etc., may be used to determine if shelves are empty or are missing a certain amount of items and need to be re-stocked.

Additional data can also be incorporated to help improve performance. For example the shelves can be lined with a known, distinct color, so visually detected color can be used in addition to depth information to detect empty shelves. Alternatively the background shelf color can be used to help calibrate and recalibrate depth sensing to achieve more accurate depth measurements.

In one embodiment, the depth sensing VCA system can be used to monitor carts moving within the store. For example, the system can sense which carts are full and which are empty. Monitoring carts can use similar height calculations using the depth sensor as described above in connection with people. For example, from an overhead sensor view, a shopping cart can be modeled as an open 3D box. A cart can be detected by its equal height rectangle boundaries. The emptiness can be measured by the average height of its inside area. As a result, retailers can better estimate what sized carts to supply, and the average volume of goods per customer. In addition, retailers can better distinguish between carts and people, and as a result, can specifically analyze the cart movement, or ignore the cart movement and focus on people movement.

Detecting whether a cart is full or not can also be used for loss prevention applications. At self-checkout lanes it may help to verify that all merchandise was removed from the cart for scanning. At checkout lanes, detecting a type of object within the shopping cart may be monitored to detect consistency with those items registered by a point of sales terminal for payment (e.g., a scanned bar code of the object input at a checkout cash register) to prevent mistakes and/or theft. For example, if a large round object is detected in the shopping cart, the system may expect to associate an item registered at the point of sales terminal with the large round object, such as a cake or pumpkin registered by the point of sales terminal. At an exit, it may detect a basket run: a person pushing a non-empty cart through the exit from the store, but not from the check out region, hence without payment.

Deliveries

In an exemplary embodiment, depth data may be used to monitor delivery of goods. For example, a video camera may be positioned to take video of a loading dock or other area where goods are delivered to a store. Delivery trucks or forklifts may be monitored so that pallets or other goods are identified as delivery objects. The video may be analyzed to confirm delivery of goods from the truck, forklift, etc. are in fact placed in an appropriate location. For example, an alert may be generated when it is detected that a forklift with pallets of goods leaves (e.g., exits the delivery area or a visual area of the video indicating the goods are not being delivered to their appropriate storage location). Depth information associated with the video may be used to classify objects as inventory in several ways. First, height information obtained of the lowermost (bottom) of goods (that may be determined from depth information) and compared to a known floor height (e.g., when they are placed on the floor during delivery). If pallets are used to carry goods, a pallet may be identified by detecting its geometric shape (e.g., typically having a square or rectangle form) and having an upper surface parallel to the floor surface. Obtained height information of the detected pallet (obtained from the depth information) may be used to confirm a pallet is placed at a certain location (e.g., floor or shelf). In addition, depth information may be used to determine that an object size corresponds to an expected pallet size. Height and/or depth information may also be used to determine appropriate delivery when the inventory height and/or depth information corresponds to respective storage location height and/or depth.

Reaching

In an exemplary embodiment, depth data and a human model are used to more reliably detect a human arm and its movement. For example, reliable detection of an arm can be used to better detect when a customer reaches across the counter.

Detecting the arm of a human is important for a range of applications. In retail, it may include, for example, reaching over the check-out lane into the till to steal money; taking items from shelves; or reaching for controlled items, such as cigarettes. Detecting arm motion only based on monocular vision is error prone, due to shadows, arms or clothing blending into the background, etc. The proposed combined system with the addition of depth and 3D information may significantly improve performance for these applications. For example, by detecting an arm height from ground, items of concern can be more easily monitored. For example, the heights of high value items, or items more prone to theft may be previously determined and associated with background image data of the video. Such items may include cigarettes in a tobacco case, alcohol, jewelry, etc. By determining an arm height appears near such items and is at the same height or close in height, improper reaching may be detected. Detected arm height may also be compared with the height of the person to confirm detection of reaching is appropriate. Improper reaching may also be detected over counters or windows into employee restricted areas and to cash registers, e.g., to detect theft.

Shopping Behavior Monitoring

The system described herein can additionally be used to determine other aspects of shoppers in a retail environment. For example, it can be used to detect size (and therefore estimate an age) of a shopper, and/or to detect shape and/or gender of a shopper.

The system can also be used to detect location of body parts and body pose and posture. This is useful to understand shopper behavior. For example, it can be used to determine where shoppers are looking and for how long, whether they are squatting down to get items on a lower shelf, or reaching up to a higher shelf, etc. Applications that determine this sort of customer behavior can include, for example, putting image sensors all over the store to monitor shopper behavior, putting image sensors on digital signage to monitor shopper attentiveness or shopper demographic information, and putting image sensors physically on shelves to monitor shopper interaction with products on shelves.

Falling or Lying Down

In one embodiment, the depth sensing VCA system can be used to detect one or more people falling in a retail store. For example, the height of portions of a human (previously detected and classified as a human) may be reviewed to determine how close portions of the human is to the floor. For example, if the head is within six inches of the floor and/or if a torso or a majority of a leg of a human is detected to be touching the ground, the human may be determined to have fallen down. A single person falling can be detected, and may be related to an emergency situation (e.g., a heart attack). As a result, an appropriate alarm can be activated. In addition, multiple people falling or lying down can be detected, which may correspond to a robbery in progress. For example, an abrupt change in height of a number of people at the same time may indicate that those people all fell to the ground at the same time and that some unusual event is occurring, which may trigger a notification (e.g., alarm) that review of the video or video environment (e.g., retail store) should be performed by management or emergency personnel. Furthermore, if those people then fail to get back up (e.g., height information continues to indicate they are on the ground), the system may determine that an event has occurred that requires assistance or further attention.

Spill Detection

Use of height information may also be used to monitor for spills, such as in a retail store. The detection of a spill may alert management of the need to clean the spill to provide better sanitary conditions and/or to avoid injury to customers. Foreground data may be extracted from background image data of frames of the image data (e.g, by determining the existence of the foreground data does not match with image data previously determined to be background image data). A blob comprised of the foreground data may be formed to detect an object in the video. The object may be initially classified as either a shadow and/or a spill if height information associated with the object indicates the height of the object is at and/or very close to floor height (e.g., within one inch or within 0.5 inches). A shadow may be distinguished from a spill if the shadow is associated with an object having a height significantly above floor height (e.g., greater than one foot above floor height). Movement (or lack of movement) of the object and correlation of movement of the object with movement of other objects may also be used to distinguish between a spill and a shadow.

2-Person Rule/Counting, Queue Length

As described previously, the depth sensing VCA system can be used to more accurately count people who are partially occluded from the camera view. For example, by using height data, the system may only need to monitor the upper part of a human body to perform the counting. Thus, the human can be monitored by detecting and tracking the maximum height value of the human. Alternatively, or in addition, only depth data (the distance from the sensor to the detected object) may be used. In an overhead sensor setting, the human head is usually the part with the closest distance to the sensor, which represents a value peak in the depth map. The human object can be monitored by detecting and tracking these depth peaks (e.g., the portion of the object having the minimum depth distance to the sensor). As a result, the detection of people is substantially less likely to be impacted by shadows and occlusions than in a system that does not include depth sensing. Use of the height and/or depth values associated with the detected people may thus assist in distinguishing one person from another, as well as tracking each person as they move in, out and/or within the store. This information can be used to count a number of people entering and/or leaving the store that may help determine store usage. This information may also be used to count a number of people in a line at the store, which may be used to determine if additional employee help is needed (e.g., to alert a manager that an additional cashier is needed).

Dwell

One embodiment may include an improved way of consistently track a human object for a long time in challenging scenarios such as crowds or illumination changes.

In an exemplary such embodiment, first, the data from depth sensor can provide the distance information of each object which will help obtain a more reliable tracking Second, the depth data makes some part of the human body easier to be detected and tracked, such as the human head and shoulder part. The system can simply detect and track human head instead of the whole person to avoid the impact of shadow and occlusions.

In a crowd scenario, by converting a perspective view of an image into a height map using the depth sensor data as described above, one can significantly reduce the complexity of the person detection and tracking because the chance of target occlusions is greatly reduced. This is also illustrated in FIG. 16, where in the normal image view, all the persons are occluding one another, while in the height map, all the human targets are separated, in which case the tracking and event detection can become easier and more reliable.

By tracking each human target individually, it is possible to monitor various activities of each person. For example, for various locations within the store, a dwell time may be determined. Thus, it may be determined that the time to wait in line on average is too long (e.g., at the deli of the store, at the pharmacy of the store, or at the check out lines of the store) by reviewing dwell times of multiple individuals (e.g., all identified adult persons visiting the store) throughout several days, weeks or months. Trends in dwell time of multiple individuals may be reviewed to determine patterns when wait times are undesirably long for customers, such as during lunch, on weekends, or during certain times throughout the year (e.g., summer time, during winter break, etc.) Dwell times of multiple individuals may be analyzed to determine the effectiveness of a product display, merchandising, and/or advertisements. Dwell time of a particular individual may be detected to be unusually long resulting in the system providing an alert to store management to send a store associate to the customer to assist the customer.

Adult Vs. Child Vs. Animal

In one embodiment, the depth sensing VCA system can be used to better count and differentiate objects in different groups. For example, the system can use height thresholds to differentiate between adults and children. This may be useful in retail environments to make more accurate correlations between sales and number of children present, or may be useful to determine which products attract greater attention by adults or children. In another embodiment, the system can be used in a home security environment to detect movement of objects in a person's home, but to filter out objects under a certain size, such as cats and small dogs.

Uses for Vehicles

The depth sensing VCA system can be used in various ways to improve analysis of vehicles. For example, it can be used to better count a number of vehicles in a store parking lot, or determine whether vehicles are speeding. The depth data can be calibrated to physical coordinates in the scene. Then, using the rate of change of depth for each vehicle tracked in the scene, the speed of the vehicle can be accurately calculated to determine whether it is speeding.

Another vehicle application is to monitor parking lots. By using a depth sensor, a surface model of one or more parking lot spaces may be created and monitored. A space emptiness measurement can be estimated to determine if each parking space is occupied. Data regarding which spaces are occupied and which are vacant can be stored and used by a central monitoring system, and can be used to keep track of parking lot capacity and availability in real-time.

In another embodiment, the depth sensing VCA system can be used to better count vehicles in general, such as for monitoring parking lot usage or traffic flow. The system may be programmed to monitor a line segment on parking lot or the road (e.g., across a road) and to monitor the depth of any objects at the line segment. When no vehicles are present, the depth of the road itself (i.e., an average distance between a depth sensor and the road surface at the designated line segment) may be determined, and a pulse, such as a binary "0" may be generated. When the detected depth of that segment changes (e.g., becomes greater than a threshold, as a result of a decreased distance between the sensor and a detected object at the designated line segment) for a period of time (which may be a short period of time required for a fast-moving vehicle to pass, or a longer period of time required for a slower-moving or longer vehicle to pass) the detected depth may indicate an object on the road for the period of time. As a result, a pulse, such as a binary "1" may be generated. The number of "1" pulses can then be recorded and used for vehicle flow analysis. In one embodiment, a camera and depth sensor are used that have a fast enough frequency (e.g., frames per second, or depth determinations per second) to accurately count vehicles moving up to a particular speed.

Depth information can also be used for vehicles to classify vehicle types at a given location. For example, different height thresholds can be set for cars versus trucks, or different widths can be set for cars versus motorcycles or bicycles. The depth information can also provide a three-dimensional volume measure instead of only a two-dimensional area measurement, which can more easily distinguish different types of vehicles.

Theft, Left Items

The depth sensing VCA system can be used to more accurately determine theft of items, or left items, in a setting. For example, a particular facility may have a certain set of items stored (e.g., a storage facility, store that is closed, etc.). The depth sensing VCA system can be used in a manner similar to vehicle flow monitoring, wherein a particular segment or area of a scene can be monitored, and an average depth of the area can be detected (e.g., an average distance between an image sensor and objects in the facility). If the average depth changes, for example if it decreases such that the average distance increases, the system can detect the difference in average distance, and may determine that an event, such as a potential theft has occurred. If the average depth increases such that the average distance decreases, the system can detect the difference in average distance, and may determine that an event, such as a potential item left behind has occurred. This can be used, for example, in airports, train stations, other transportation facilities or other public areas to monitor for suspicious items left where they are not supposed to be. In one embodiment, it can be used to detect rail theft of palettes removed from the system.

Odd/Suspicious Behavior

Security personnel are generally trained to look for certain behavior in people. Using the depth sensing VCA system, the system itself can recognize these behaviors and trigger alarms in response. For example, the system can look for erratic movements by monitoring fast changes in depth due to particular objects, or can better detect loitering using depth sensing. As another example, a camera sensor can recognize when a severe change in depth of an object has occurred, such as an event that coincides with a person covering the camera with an object to obscure the camera's view. Such an event can trigger an alarm.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present disclosure.

What is claimed is:

1. A method of monitoring a retail environment comprising:
   taking a video at a store with a video sensor, the video comprising a plurality of frames, each frame including two-dimensional (2D) image data;
   for each frame, receiving depth data associated with the 2D image data, the depth data corresponding to one or more distances from the video sensor to features represented by the 2D image data;
   analyzing the 2D image data without analyzing the depth data to detect one or more objects in the video;
   using the depth data to classify the one or more detected objects in the store depicted in the video, classification of the one or more detected objects comprising at least one of person classification and inventory classification and being based on a volume of the one or more detected objects; and
   detecting an event of the classified one or more objects, wherein the volume is determined by using the depth data along with the 2D image data to determine a plurality of convex hull slices on different Z-planes, and by summing areas of the plurality of convex hull slices.

2. The method of claim 1,
   wherein the classification of the one or more objects comprises person classification, and
   wherein the detecting an event of the classified one or more objects comprises using the depth data to detect a detected person is lying down in the store.

3. The method of claim 2, wherein the detection of a person lying down comprises identifying one or more parts of the detected person and comparing height information of the one or more parts of the detected person with a height of the floor of the store.

4. The method of claim 1, wherein the detecting an event of the classified one or more objects comprises using the depth data associated with the 2D image data to detect a spill of a substance on a floor of the store.

5. The method of claim 4, wherein the detection of a spill comprises obtaining height information of a first object and determining that the height information indicates the first object is within a first distance of the height of the floor.

6. The method of claim 1,
   wherein analyzing the 2D image data and using the depth data to classify the one or more objects detects and classifies plural objects, each as a respective person, and
   wherein the detecting of the event comprises counting a number of people.

7. The method of claim 6, further comprising monitoring at least one of a height and a distance from a depth sensor providing the depth data of an upper portion of each object classified person.

8. The method of claim 7, further comprising:
   for each of the objects classified as a person, associating a depth value with a portion of the person most distant from the floor of the store.

9. The method of claim 7, further comprising determining a height value of each object classified as a person, and using the height value to track each object classified as a person.

10. The method of claim 9, wherein the detecting of the event comprises counting a number of people entering the store.

11. The method of claim 9, wherein the detecting of the event comprises counting a number of people in a line of the store.

12. The method of claim 1, wherein using the depth data to classify the one or more objects comprises obtaining height data of at least some of the detected one or more objects from corresponding depth data of the at least some of the detected one or more objects.

13. The method of claim 12, wherein the height data is used to classify a person as an adult.

14. The method of claim 13, wherein the height data is used to classify a person as a child.

15. The method of claim 12, wherein the height data is used to classify an object as an object located in a shopping cart.

16. The method of claim 15, further comprising classifying a type of the object located in the shopping cart.

17. The method of claim 12, wherein the height data is used to classify an object as a shopping cart.

18. The method of claim 17, further comprising tracking shopping cart movement within the store.

19. The method of claim 1, wherein a first object is classified as a person, and detecting an event of the person comprises detecting a reaching of the person.

20. The method of claim 19, wherein detecting the reaching of the person comprises detecting an arm height of the person from the depth data.

21. The method of claim 20, wherein detecting the reaching of the person comprises comparing the detected arm height of the person with a known height of a background feature represented by the image data.

22. The method of claim 1, wherein a first object is classified as a person, and detecting an event of the person comprises detecting a time the person dwells within a certain location within the store.

23. The method of claim 22, further comprising generating an alert in response to detecting that the person has dwelled within a certain location greater than a predetermined time.

24. The method of claim 22, further comprising analyzing dwell times of multiple customers over plural weeks to determine a pattern of dwell times of customers of the store.

25. The method of claim 24, further comprising using the pattern of dwell times to determine employee allocation within the store.

26. The method of claim 24, further comprising using the pattern of dwell times to adjust merchandising within the store.

27. The method of claim 1, wherein a first object is classified as inventory, and detecting an event of the inventory comprises detecting that the inventory is low or absent.

28. The method of claim 27, wherein the depth data is used to determine a depth of the inventory on a shelf, within a refrigerator, or within a freezer in the store, and wherein the depth data is used to detect that the inventory is low or absent.

29. The method of claim 28, further comprising generating an alert in response to determining that the inventory is low or absent to notify at least one of store management or inventory suppliers of the need to supplement the inventory.

30. The method of claim 1, wherein a first object is classified as inventory, and detecting an event of the inventory comprises detecting that the inventory is delivered at a delivery location of the store.

31. The method of claim 30, wherein the depth data is used to detect appropriate delivery of inventory to the store.

32. The method of claim 1, wherein a first object is classified as inventory, and detecting an event of the inventory comprises tracking the inventory to detect if the inventory is removed without delivery.

* * * * *

UNITED STATES PATENT AND TRADEMARK OFFICE
CERTIFICATE OF CORRECTION

PATENT NO. : 9,740,937 B2  
APPLICATION NO. : 13/744251  
DATED : August 22, 2017  
INVENTOR(S) : Zhang et al.

Page 1 of 1

It is certified that error appears in the above-identified patent and that said Letters Patent is hereby corrected as shown below:

In the Specification  
Column 14, Line 33, "situation 310" should read --situation 1310--.  
Column 14, Line 45, "situation 320" should read --situation 1320--.  
Column 14, Line 50, "situation 330" should read --situation 1330--.  
Column 15, Line 4, "each of these examples (320 and 330)" should read --each of these examples (1320 and 1330)--.

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*